(12) United States Patent
Dart et al.

(10) Patent No.: US 12,066,443 B2
(45) Date of Patent: *Aug. 20, 2024

(54) METHOD OF TREATING ACUTE CORONARY SYNDROME

(71) Applicants: ALFRED HEALTH, Melbourne (AU); PEKING UNIVERSITY THIRD HOSPITAL, Beijing (CN)

(72) Inventors: Anthony Dart, Melbourne (AU); Wei Gao, Beijing (CN)

(73) Assignees: Alfred Health, Melbourne (AU); Peking University Third Hospital, Beijing (CN)

( * ) Notice: Subject to any disclaimer, the term of this patent is extended or adjusted under 35 U.S.C. 154(b) by 681 days.

This patent is subject to a terminal disclaimer.

(21) Appl. No.: 16/651,860

(22) PCT Filed: Sep. 27, 2018

(86) PCT No.: PCT/AU2018/051059
§ 371 (c)(1),
(2) Date: Mar. 27, 2020

(87) PCT Pub. No.: WO2019/060960
PCT Pub. Date: Apr. 4, 2019

(65) Prior Publication Data
US 2020/0256878 A1    Aug. 13, 2020

(30) Foreign Application Priority Data

Sep. 30, 2017  (WO) ................ PCT/CN2017/104752

(51) Int. Cl.
| | |
|---|---|
| G01N 33/68 | (2006.01) |
| A61B 5/00 | (2006.01) |
| A61B 5/02 | (2006.01) |
| G16H 10/40 | (2018.01) |
| G16H 40/63 | (2018.01) |
| G16H 50/20 | (2018.01) |
| G16H 50/30 | (2018.01) |
| G16H 50/70 | (2018.01) |
| G16H 70/60 | (2018.01) |

(52) U.S. Cl.
CPC .......... *G01N 33/6893* (2013.01); *A61B 5/02* (2013.01); *A61B 5/7275* (2013.01); *G16H 10/40* (2018.01); *G16H 40/63* (2018.01); *G16H 50/20* (2018.01); *G16H 50/30* (2018.01); *G16H 50/70* (2018.01); *G16H 70/60* (2018.01); *G01N 2333/4712* (2013.01); *G01N 2333/52* (2013.01); *G01N 2333/58* (2013.01); *G01N 2800/324* (2013.01); *G01N 2800/50* (2013.01); *G01N 2800/52* (2013.01)

(58) Field of Classification Search
CPC ....... G01N 33/6893; G01N 2333/4712; G01N 2333/52; G01N 2333/58; G01N 2800/324; G01N 2800/50; G01N 2800/52; A61B 5/02; A61B 5/7275; G16H 10/40; G16H 40/63; G16H 50/20; G16H 50/30; G16H 50/70; G16H 70/60
See application file for complete search history.

(56) References Cited

U.S. PATENT DOCUMENTS

| | | |
|---|---|---|
| 2005/0054117 A1 | 3/2005 | Giroir et al. |
| 2006/0034832 A1 | 2/2006 | Kimura et al. |
| 2008/0118924 A1 | 5/2008 | Buechler |
| 2011/0144914 A1 | 6/2011 | Harrington et al. |
| 2014/0234861 A1 | 8/2014 | Dart |
| 2015/0065372 A1 | 3/2015 | Amir et al. |
| 2020/0264196 A1 | 8/2020 | Dart et al. |

FOREIGN PATENT DOCUMENTS

| | | |
|---|---|---|
| EP | 1983058 A1 | 10/2008 |
| WO | 2005/071407 A2 | 8/2005 |
| WO | 2006/001813 A2 | 1/2006 |
| WO | 2007/110359 A1 | 10/2007 |
| WO | 2007/140188 A2 | 12/2007 |
| WO | 2009/017405 A2 | 2/2009 |
| WO | 2011/026017 A1 | 3/2011 |
| WO | 2011/032109 A1 | 3/2011 |
| WO | 2013/023233 A1 | 2/2013 |
| WO | 2019/060960 A1 | 4/2019 |
| WO | 2019/061396 A1 | 4/2019 |

OTHER PUBLICATIONS

Jian, et al.; GW25-e2426 Characterization of bi-ventricular coronary flow reserve and remodeling in mice with pressure overload cardiac hypertrophy; JACC; vol. 64/16/Suppl C; GW-ICC Abstracts/Basic and Translational Medicine; Oct. 2014; 1 pg.

Raybiotech, Inc.; RayBio® Label-based (L-Series) Human Antibody Array 1000 Membrane Kit, A combination of Human L-507 and Human L-493 Arrays; Patent Pending Technology User Manual; Feb. 27, 2014; 26 pgs.

European Patent Office; Supplementary European Search Report and Opinion; EP App. 18860129; Jun. 10, 2021; 6 pgs.

T. Roger, et al; Plasma Levels of Macrophage Migration Inhibitory Factor and D-Dopachrome Tautomerase Show a Highly Specific Profile in Early Life; Frontiers in Immunology; 2017; pp. 1-10; vol. 8, article 28.

(Continued)

*Primary Examiner* — Olga N Chernyshev
(74) *Attorney, Agent, or Firm* — Kilpatrick Townsend & Stockton LLP

(57) ABSTRACT

The invention relates to a method for prognosing ACS in a subject, the method comprising determining plasma MIF and Nt-proBNP (or BNP) concentrations in a sample from the subject, diagnosing ACS when the subject plasma concentrations are greater than a reference MIF and Nt-proBNP (or BNP) plasma concentration, and prognosing the magnitude of ACS from the subject plasma MIF and Nt-proBNP (or BNP) concentrations. Also provided is a method of treating ACS in a subject, a device, a kit, and a cardiac biomarker related to the methods of prognosing ACS.

14 Claims, 6 Drawing Sheets
Specification includes a Sequence Listing.

(56) References Cited

OTHER PUBLICATIONS

P. Kavsak, et al; Risk Stratification for Heart Failure and Death in an Acute Coronary Syndrome Population Using Inflammatory Cytokines and N-Terminal Pro-Brain Natriuretic Peptide; Clinical Chemistry; 2007; 2112-2118; 53:12.

Achar, S., et al.; Diagnosis of Acute Coronary Syndrome; American Family Physician; 2005, vol. 72, pp. 119-126.

Chan, W., et al; Macrophage migration inhibitory factor or the early prediction of infarct size; Jour. Amer. Heart Assoc.; 2013; 2.5; e000226.

Chan, W., et al; Acute left ventricular remodeling following myocardial infarction: coupling of regional healing with remote extracellular matrix expansion; JACC: Cardiovascular Imaging; 2012; 5.9; pp. 884-893.

Cho, et al; The Utility of point-of-care biomarkers as a prognostic tool for patients with acute coronary syndromes; Signa Vitae; 2017; 13(1); pp. 89-94.

Dandona, et al; Increased Plasma Concentration of Macrophage Migration Inhibitory Factor (MIF) and MIF mRNA in Mononuclear Cells in the Obese and the Suppressive Action of Metformin; J. Clin. Endocrinol. Metab.; Oct. 2004; 89(10):5043-7.

Deng, et al; Admission macrophage migration inhibitory factor predicts long-term prognosis in patients with ST segment elevation myocardial infarction; Eur. Heart Jour.—Quality of Care and Clinical Outcomes; Jul. 1, 2018; (published online: May 2, 2018), 4.3, pp. 208-219.

Deng, et al; Admission macrophage migration inhibitory factor predicts long-term prognosis in patients with ST segment elevation myocardial infarction; Jour. Amer. College of Cardiology; Mar. 20, 2018; 71.11; Suppl. A240, Presentation No. 1305-451.

Deng; Research into changes in blood MIF levels in early stage of onset in STEMI patients and correlation between such changes and long-term prognosis; Peking University Health Science Center Clinical/Oral Medicine Professional Doctorate Student; May 23, 2018; translation (2 pgs.).

Ganame, et a; Impact of myocardial haemorrhage on left ventricular function and remodeling in patients with reperfused acute myocardial infarction; European Heart Jour.; 2009; 104(13):1483-1488.

Gao, et al; Macrophage migration inhibitory factor (MIF), a novel biomarker and player in acute myocardial infarction (AMI); Heart, Lung and Circulation; 2012; 21 Suppl. S44, Abstract 104.

Li, et al; Macrophage migration inhibitory factor in predicting short-and long-term major adverse cardiovascular events in patients with ST-segment elevation myocardial infarction; Jour. Amer. College of Cardiology; 2014; 64, 16, Suppl. C, C61, Abstract GW25-e2515.

Mayeux, et al; Biomarkers: Potential Uses and Limitations; NeuroRX; Apr. 2004; vol. 1(2):182-8.

McCord, et al.; Ninety-minute exclusion of acute myocardial infarction by use of quantitative point-of-care testing of myoglobin and troponin; i. Circulation; 2001; 104(13):1483-1488.

Muller, et al; Macrophage Migration Inhibitory Factor is Enhanced in Acute Coronary Syndromes and is Associated with the Inflammatory Response; PLOS One; Jun. 5, 2012; vol. 77, No. 6/e38376; pp. 1-7.

Omland, et al; N-Terminal Pro-B-Type Natriuretic Peptide and Long-Term Mortality in Acute Coronary Syndromes; Circulation; Dec. 3, 2002; vol. 106, No. 23; pp. 2913-2918.

Piot, et al; Effect of cyclosporine on reperfusion injury in acute myocardial infarction; New England Jour. of Medicine; 2008; 359(5):473-481.

Richards, et al; B-Type Natriuretic Peptides and Ejection Fraction for Prognosis After Myocardial Infarction; Circulation; Jun. 10, 2003; vol. 107, No. 22; pp. 2786-2792.

Seropian, et al; Inflammatory markers in ST-elevation acute myocardial infarction; Eur. Heart Jour.: Acute cardiovascular Care; 2016; 5.4; 382-395.

Sprong, et al; Macrophaage Migration Inhibitory Factor (MIF) in Meningococcal Septic Shock and Experimental Human Endotoxemia; Shock; 2007; vol. 27, No. 5; pp. 482-487.

Than, et al; A 2-h diagnostic protocol to assess patients with chest pain symptoms in the Asia-Pacific region (ASPECT): a prospective observational validation study; Lancet, 2011; 88(7):774-777.

Tuxunguli, et al; Association study of plasma NT-proBNP levels and severity of acute coronary syndrome; Genet. Mol. Res.; 2014;13(3):5754-5757.

Yu, et al; Elevation of plasma concentration of macrophage migration inhibitory factor in patients with acute myocardial infarction; American Jour. of Cardiology; 2001; 88:774-777.

Waiker, et al; Imperfect Gold Standards for Kidney Injury Biomarker Evaluation; J. Am. Soc. Nephrol.; Jan. 2012; 23(1):13-21.

Zhao, et al; Validity of plasma macrophage migration inhibitory factor for diagnosis and prognosis of hepatocellular carcinoma; Int. J. Cancer; Nov. 2011; 129(10):2463-72; Epub Apr. 20, 2011.

State Intellectual Property Office of the P.R. China; International Search Report; mailed Jul. 5, 2018 in PCT/CN2017/104752; 4 pgs.

Australian Patent Office; International Preliminary Report on Patentability; dated Dec. 10, 2013 in PCT/AU2011/001027 (5 pgs.).

Australian Patent Office; International Search Report; dated Sep. 14, 2011 in PCT/AU2011/001027 (3 pgs).

Buchner, S. et al., "Dynamic changes in N-terminal pro-brain natriuretic peptide in acute coronary syndromes treated with percutaneous coronary intervention: a marker of ischemic burden, reperfusion and outcome," Clin Chem Lab Med, 48(6):875-81, 2010.

Coppola, G. et al., "Analysis of N-terminal pro-B-type natriuretic peptide in patients with acute coronary syndromes," Coronary Artery Disease, 20(3):225-29, 2009.

Giannitsis, E. et al., "High-sensitivity cardiac troponin T and N-terminal pro-B-type natriuretic peptide predict mortality in stable coronary artery disease: results from the Ludwigshafen Risk and Cardiovascular Health (LURIC) study," Clin Chem Lab Med, 51(10):2019-28, 2013.

Hogenhuis, J. et al., "Influence of age on natriuretic peptides in patients with chronic heart failure: a comparison between ANP/NT-ANP and BNP/NT-proBNP," The European Journal of Heart Failure, 7(1):81-86, 2005.

Ino, Y. et al., "Difference of culprit lesion morphologies between ST-segment elevation myocardial infarction and non-ST-segment elevation acute coronary syndrome: an optical coherence tomography study," JACC: Cardiovascular Interventions, 4(1):76-82, 2011.

Ishihara, M. et al., "Clinical Presentation, Management and Outcome of Japanese Patients With Acute Myocardial Infarction in the Troponin Era—Japanese Registry of Acute Myocardial Infarction Diagnosed by Universal Definition (J-MINUET)—," Circulation Journal, 79(6): 1255-62, 2015.

Masson, S. et al., "Direct comparison of B-type natriuretic peptide (BNP) and amino-terminal proBNP in a large population of patients with chronic and symptomatic heart failure: the Valsartan Heart Failure (Val-HeFT) data," Clinical Chemistry, 52(8):1528-38, 2006.

Mueller, T. et al., "Diagnostic accuracy of B type natriuretic peptide and amino terminal proBNP in the emergency diagnosis of heart failure," Heart, 91(5):606-12, 2005.

Pfister, R. et al., "Use of NT-proBNP in routine testing and comparison to BNP," The European Journal of Heart Failure, 6(3):289-93, 2004.

Richards, M. et al., "Plasma N-terminal pro-brain natriuretic peptide and adrenomedullin: new neurohormonal predictors of left ventricular function and prognosis after myocardial infarction," Circulation, 97(19):1921-29, 1998.

Weber, M. and C. Hamm, "Role of B-type natriuretic peptide (BNP) and NT-proBNP in clinical routine," Heart, 92(6):843-49, 2006.

SEQUENCE LISTING

```
<160> NUMBER OF SEQ ID NOS: 1

<210> SEQ ID NO 1
<211> LENGTH: 114
<212> TYPE: PRT
<213> ORGANISM: Homo sapiens

<400> SEQUENCE: 1

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Gln Asn Arg Ser Tyr Ser Lys Leu Leu Cys
65                  70                  75                  80

Gly Leu Leu Ala Glu Arg Leu Arg Ile Ser Pro Asp Arg Val Tyr Ile
                85                  90                  95

Asn Tyr Tyr Asp Met Asn Ala Ala Asn Val Gly Trp Asn Asn Ser Thr
            100                 105                 110

Phe Ala
```

METHOD OF TREATING ACUTE CORONARY SYNDROME

CROSS REFERENCE TO RELATED APPLICATIONS

The present application is a § 371 National Phase Application of PCT/AU2018/051059, filed Sep. 27, 2018, which claims priority from PCT/CN2017/104752, filed Sep. 30, 2017, the disclosures of which are hereby incorporated by reference in their entireties for all purposes herein.

SEQUENCE LISTING PROVIDED AS ASCII FORMAT FILE

This application contains a Sequence Listing submitted electronically in ASCII format and is herein incorporated by reference in its entirety. Said ASCII copy, created on May 6, 2024, is named 102504_1176402_SEQ_LST.txt and is 1,427 bytes in size.

CROSS REFERENCE TO RELATED APPLICATION

This application claims priority from PCT/CN2017/104752, the contents of which are hereby incorporated in their entirety.

FIELD OF THE INVENTION

The invention relates to a method for prognosing acute coronary syndrome, and a cardiac biomarker for use in the methods. The invention also relates to a device and a kit for use according to the methods.

BACKGROUND OF THE INVENTION

The use of plasma biomarkers has become central to the diagnosis and prognosis of cardiovascular events. For example, the prognostic impact of myoglobin elevation among patients with coronary artery disease (CAD) is well established.

Current therapies and timely primary percutaneous coronary intervention (PCI) have significantly improved the prognosis of patients with ST-segment elevated myocardial infarction (STEMI) during the last few decades. However, recurrent major adverse cardiovascular events (MACE) after STEMI remains common. Early risk stratification of patients with high risk of long-term MACE is critical for allocation of aggressiveness of therapy and intensity of care to improve their prognosis.

Existing plasma biomarkers that can be utilised to diagnose and/or prognose STEMI or acute coronary syndrome include myoglobin, creatine kinase-MB (CK-MB), and troponin. Each of these plasma biomarkers however are associated with problems. For instance, whilst myoglobin peaks in plasma approximately 2 hours after a cardiac event, it has low cardiac-specificity. Also, whilst CK peaks in plasma approximately 10 hours after a cardiac event, cumulative plasma CK concentrations are not available until at least 48 hours after the cardiac event. Furthermore, CK is not cardiac-specific.

Troponin has become the predominant plasma biomarker for the early detection of acute coronary syndrome such as myocardial necrosis, and has largely superseded the measurement of CK. The single measurement of plasma troponin is one of the most sensitive and specific tests for myocardial necrosis at present. Whilst current evidence suggests that a low single admission troponin can be used to exclude (rule out) a diagnosis of ACS in subjects with a low a probability of ACS, most patients require serial measures over 6 or more hours to safely exclude such a diagnosis.

Therefore, there is a need for a new or improved method for prognosing acute coronary syndrome.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method for providing a prognosis of acute coronary syndrome (ACS) in a subject comprising:
  determining the concentration of
    (a) macrophage migration inhibitory factor (MIF) or a fragment thereof, and
    (b) N-terminal prohormone of brain natriuretic peptide (Nt-proBNP) or a fragment thereof,
    in a sample from the subject,
  and
  prognosing ACS when the subject plasma MIF and Nt-proBNP concentration is greater than a reference plasma MIF and a reference plasma Nt-proBNP concentration.

The present invention provides a method for providing a prognosis of acute coronary syndrome (ACS) in a subject comprising:
  determining the concentration of
    (a) macrophage migration inhibitory factor (MIF) or a fragment thereof, and
    (b) B-type natriuretic peptide (BNP) or a fragment thereof,
    in a sample from the subject,
  and
  prognosing ACS when the subject plasma MIF and BNP concentration is greater than a reference plasma MIF and a reference plasma BNP concentration.

The present invention also provides a method for providing a prognosis of a subject having ACS, the method comprising
  determining the concentration of
    (a) macrophage migration inhibitory factor (MIF) or a fragment thereof, and
    (b) N-terminal prohormone of brain natriuretic peptide (Nt-proBNP) or a fragment thereof,
    in a sample from the subject,
  comparing the concentration of MIF to a reference MIF concentration,
  comparing the concentration of Nt-proBNP to a reference Nt-proBNP concentration,
  wherein the concentration of MIF and Nt-proBNP compared to their respective reference concentrations is indicative of the subject's prognosis.

The present invention also provides a method for providing a prognosis of a subject having ACS, the method comprising
  determining the concentration of
    (a) macrophage migration inhibitory factor (MIF) or a fragment thereof, and
    (b) B-type natriuretic peptide (BNP) or a fragment thereof,
    in a sample from the subject, comparing the concentration of MIF to a reference MIF concentration, comparing the concentration of BNP to a reference BNP concentration, wherein the concentration of MIF and BNP compared to their respective reference concentrations is indicative of the subject's prognosis.

The present invention also provides a method for providing a prognosis of a subject having ACS, the method comprising determining the concentration of
(a) macrophage migration inhibitory factor (MIF) or fragment thereof, and
(b) N-terminal prohormone of brain natriuretic peptide (Nt-proBNP) or a fragment thereof
in a sample from the subject, comparing the concentration of MIF to a reference MIF concentration, comparing the concentration of Nt-proBNP to a reference Nt-proBNP concentration, wherein the reference concentrations of MIF and Nt-proBNP are concentrations below which correlate with an increased probability of survival and a decreased probability of non-fatal cardiac events at a later time, and above which correlate with a decreased probability of survival and an increased probability of non-fatal cardiac events at a later time, thereby providing a prognosis of a subject having ACS.

The present invention also provides a method for providing a prognosis of a subject having ACS, the method comprising determining the concentration of
(c) macrophage migration inhibitory factor (MIF) or fragment thereof, and
(d) B-type natriuretic peptide (BNP) or a fragment thereof
in a sample from the subject, comparing the concentration of MIF to a reference MIF concentration, comparing the concentration of BNP to a reference BNP concentration, wherein the reference concentrations of MIF and BNP are concentrations below which correlate with an increased probability of survival and a decreased probability of non-fatal cardiac events at a later time, and above which correlate with a decreased probability of survival and an increased probability of non-fatal cardiac events at a later time, thereby providing a prognosis of a subject having ACS.

The present invention also provides a method for providing a prognosis of a subject having ACS, the method comprising analysing levels of (a) macrophage migration inhibitory factor (MIF) or fragment thereof, and (b) N-terminal prohormone of brain natriuretic peptide (Nt-proBNP) or a fragment thereof, in a sample from the subject, determining the concentration of MIF or fragment thereof and Nt-proBNP or a fragment thereof in the sample from the subject, comparing the concentration of MIF or fragment thereof to a reference MIF concentration, comparing the concentration of Nt-proBNP or fragment thereof to a reference Nt-proBNP concentration, assigning the subject to a risk group based on whether the concentration of MIF or fragment thereof is higher or lower than the reference concentration, and whether the concentration of Nt-proBNP or fragment thereof is higher or lower than the reference concentration, wherein a concentration of MIF or fragment thereof that is higher than the reference MIF concentration indicates a low likelihood of survival and/or high likelihood of non-fatal cardiac events, wherein a concentration of Nt-proBNP or fragment thereof that is higher than the reference Nt-proBNP concentration indicates a low likelihood of survival and/or high likelihood of non-fatal cardiac events, thereby providing a prognosis of a subject having ACS.

The present invention also provides a method for providing a prognosis of a subject having ACS, the method comprising analysing levels of (a) macrophage migration inhibitory factor (MIF) or fragment thereof, and (b) B-type natriuretic peptide (BNP) or a fragment thereof, in a sample from the subject, determining the concentration of macrophage migration inhibitory factor (MIF) or fragment thereof and B-type natriuretic peptide (BNP) or a fragment thereof in the sample from the subject, comparing the concentration of MIF or fragment thereof to a reference MIF concentration, comparing the concentration of BNP or fragment thereof to a reference BNP concentration, assigning the subject to a risk group based on whether the concentration of MIF or fragment thereof is higher or lower than the reference concentration, and whether the concentration of BNP or fragment thereof is higher or lower than the reference concentration, wherein a concentration of MIF or fragment thereof that is higher than the reference MIF concentration indicates a low likelihood of survival and/or high likelihood of non-fatal cardiac events, wherein a concentration of BNP or fragment thereof that is higher than the reference BNP concentration indicates a low likelihood of survival and/or high likelihood of non-fatal cardiac events, thereby providing a prognosis of a subject having ACS.

In an aspect of the invention, the reference concentration of MIF, Nt-proBNP (or BNP) and/or troponin is determined from a reference concentration of a plasma, blood or serum sample obtained from at least one individual previously identified as suffering from ACS.

The present invention also provides a method for providing a prognosis of a subject having ACS, the method comprising determining the concentration of macrophage migration inhibitory factor (MIF) or a fragment thereof in a sample from the subject, wherein if the concentration of MIF from the sample from the subject is equal to or higher than about 70 ng/ml the subject is determined to have a decreased probability of survival and an increased probability of non-fatal cardiac events at a later time, wherein if the concentration of MIF from the sample from the subject is lower than about 70 ng/ml the subject is determined to have an increased probability of survival and a decreased probability of non-fatal cardiac events at a later time, thereby providing a prognosis of a subject having ACS.

In an aspect of the invention, if the concentration of MIF from the sample from the subject is equal to or higher than 73 ng/ml, the subject is determined to have a decreased probability of survival and an increased probability of non-fatal cardiac events at a later time. Moreover, if the concentration of MIF from the sample from the subject is lower than about 73 ng/ml, the subject is determined to have an increased probability of survival and a decreased probability of non-fatal cardiac events at a later time.

The present invention also provides a method for providing a prognosis of a subject having ACS, the method comprising determining the concentration of macrophage migration inhibitory factor (MIF) or a fragment thereof in a sample from the subject, comparing the concentration of MIF to reference MIF concentrations of about 40 ng/ml and about 70 ng/ml, wherein if the concentration of MIF from the sample from the subject is equal to or lower than about 40 ng/ml the subject is determined to have a high probability of survival and a low probability of non-fatal cardiac events at a later time, wherein if the concentration of MIF from the sample from the subject is equal to or higher than about 70 ng/ml the subject is determined to have a low probability of survival and a high probability of non-fatal cardiac events at a later time, thereby providing a prognosis of a subject having ACS.

In an aspect of the invention, the method comprises comparing the concentration of MIF to reference MIF concentrations of about 40 ng/ml and about 73 ng/ml, wherein if the concentration of MIF from the sample from the subject is equal to or higher than about 73 ng/ml the subject is determined to have a low probability of survival and a high probability of non-fatal cardiac events at a later time.

In any aspect of the invention, the prognosis is of survival, preferably long term survival, or non-fatal cardiac events. Survival may be selected from MACE-Free survival, all-cause mortality free survival, cardiac death free survival or heart failure (HF) rehospitalisation free survival, or any other survival described herein. Non-fatal cardiac events may include MACE, impaired restoration of myocardial reperfusion, and adverse improvement of LVEF.

In any aspect of the invention, the prognosis may be indicative of survival 1, 2, 4, 6, 8, 10, 12, 14, 16, 18, 20, 22, 24, 26, 28, 30, 32, 34, 36, 28, 40, 42, 44, 46, 48, 50, 52, 54, 56, 58, 60, 62, 64, 66, 68, 70, 72, 74, 76, 78, 80 or more, months following diagnosis of ACS.

In any aspect of the invention, the present invention further comprises determining the concentration of troponin or a fragment thereof. Preferably, the troponin is high sensitive-troponin T (hs-TnT). The method also further comprises comparing the concentration of troponin or a fragment thereof to a reference troponin concentration. The reference concentration of troponin is a concentration below which correlates with an increased probability of survival and a decreased probability of non-fatal cardiac events at a later time, and above which correlates with a decreased probability of survival and an increased probability of non-fatal cardiac events.

In any aspect of the invention, the concentration of either BNP, or a fragment thereof, or N-terminal prohormone of brain natriuretic peptide (Nt-proBNP), or a fragment thereof, may be measured, analysed or determined. BNP is synthesized as a 134-amino acid preprohormone (preproBNP), encoded by the human gene NPPB. Removal of the 25-residue N-terminal signal peptide generates the prohormone, proBNP, which is stored intracellularly as an O-linked glycoprotein; proBNP is subsequently cleaved between arginine-102 and serine-103 by a specific convertase into Nt-proBNP and the biologically active 32-amino acid polypeptide BNP, which are secreted into the blood in equimolar amounts.

In any aspect of the invention, the method comprises determining the concentrations of MIF, Nt-proBNP (or BNP) and/or troponin from plasma, blood or serum. Preferably, the method comprises determining the concentrations of MIF, Nt-proBNP and/or troponin from plasma.

In any aspect of the invention, the method may not include a step of obtaining a sample of plasma, blood or serum from a subject. In other words, the method includes determining the concentrations of MIF, Nt-proBNP (or BNP) and/or troponin from plasma, blood or serum sample previously obtained from a subject, i.e. obtained at a time before a method of the invention is performed. Further, the sample of plasma, blood or serum may be an in vitro sample of plasma, blood or serum.

In any aspect of the invention, the acute coronary syndrome is acute myocardial infarction (AMI). The AMI may be ST elevation myocardial infarction (STEMI) or non-ST elevation myocardial infarction (non-STEMI). Preferably, the AMI is STEMI. In some embodiments, the subject with STEMI may have been treated with primary percutaneous coronary intervention (PCI).

In any aspect of the invention, the method further comprises performing a step of performing percutaneous coronary intervention (PCI) and/or thrombolysis on the subject. Preferably, the performing a step of performing percutaneous coronary intervention (PCI) and/or thrombolysis is only performed on those subjects identified as having a poor prognosis, or in other words, a decreased or low likelihood of survival and/or an increased or high likelihood of non-fatal cardiac events.

In any aspect of the invention, the method comprises determining MIF concentrations in a sample taken less than 4 hours after symptom onset or hospital admission. Alternatively, a MIF sample may be taken from a subject obtained 210 minutes, 180 minutes, 150 minutes, 120 minutes, 110 minutes, 100 minutes, 90 minutes, 80 minutes, 70 minutes, 60 minutes, 50 minutes, 40 minutes, 30 minutes, 20 minutes, 10 minutes or 5 minutes or less after symptom onset or hospital admission.

In any aspect of the invention, the method comprises determining Nt-proBNP or BNP concentration in a sample taken about, or between, any of the following: 0.5 days, 1.0 day, 1.5 days, 2.0 days, 2.5 days, 3.0 days, 3.5 days, 4.0 days, 4.5 days, 5.0 days, 5.5 days, 6.0 days, 6.5 days or more after symptom onset or hospital admission. Preferably, Nt-proBNP or BNP concentrations are determined in a sample obtained from a patient about 3 days following symptom onset or hospital admission.

In any aspect of the invention, the method comprises determining troponin concentration in a sample taken about, or between, any of the following: 0.5 days, 1.0 day, 1.5 days, 2.0 days, 2.5 days, 3.0 days, 3.5 days, 4.0 days, 4.5 days, 5.0 days, 5.5 days, 6.0 days, 6.5 days, 7.0 days, 7.5 days, 8.0 days, 8.5 days, 9.0 days, 9.5 days, 10.0 days, 10.5 days, 11 days, 11.5 days, 12 days or more after symptom onset or hospital admission. Preferably, the troponin is high sensitive-troponin T (hs-TnT).

In any aspect of the invention, the concentration of MIF, Nt-proBNP or BNP, and troponin are determined in the same sample. Alternatively, Nt-proBNP or BNP, troponin and MIF may be determined from different samples.

The present invention provides a method of providing a prognosis of a subject following a diagnosis of acute coronary syndrome (ACS) comprising determining the concentration of macrophage migration inhibitory factor (MIF) and N-terminal prohormone of brain natriuretic peptide (Nt-proBNP) or a fragment thereof in a sample from the subject, and prognosing ACS when the subject MIF and Nt-proBNP concentration is greater than a reference MIF and Nt-proBNP concentration.

In any aspect of the invention, the method comprises determining whether the concentration of MIF falls within the concentration range of between about 40 ng/ml to 70 ng/ml, less than about 40 ng/ml or more than about 70 ng/ml. In any aspect of the invention, a MIF concentration of equal to, or more than about 70 ng/ml is associated with the worst prognosis. In another aspect, a MIF concentration equal to or more than about 73 ng/ml is associated with the worst prognosis. In any aspect of the invention, the reference concentration may be 40 ng/ml, 70 ng/ml, 73 ng/ml or any one of the concentrations described herein, particularly in Table 2. Determining the concentration of MIF may be by any assay known in the art, including the assays described herein.

In any aspect of the invention, the method comprises determining whether the concentration of hs-TnT falls within the range of about 2.5 ng/ml to about 4.5 ng/ml, equal to or less than about 2.5 ng/ml, or equal to or more than about 4.5 ng/ml. Preferably, a hs-TnT concentration of equal to or more than about 4.5 ng/ml is associated with the worst prognosis. In any aspect of the invention, the reference concentration may be 2.5 ng/ml, 4.5 ng/ml or any one of the concentrations described herein, particularly in Table 2. Determining the concentration of hs-TnT may be by any assay known in the art, including the assays described herein.

In any aspect of the invention, the method comprises determining whether the concentrations of Nt-proBNP fall within the range of between about 700 pg/ml to about 1200 pg/ml, equal to or less than about 700 pg/ml, or equal to or more than about 1200 pg/ml. Preferably, a concentration of Nt-proBNP more than about 1200 pg/ml is associated with the worst prognosis. In any aspect of the invention, the reference concentration may be 700 pg/ml, 1200 pg/ml or any one of the concentrations described herein, particularly in Table 2. Determining the concentration of Nt-proBNP may be by any assay known in the art, including the assays described herein.

The present invention also provides a method of treating acute coronary syndrome (ACS) in a subject, the method comprising:
  determining macrophage migration inhibitory factor (MIF) or fragment thereof and N-terminal prohormone of brain natriuretic peptide (Nt-proBNP) or fragment thereof concentration in a sample taken from the subject, and prognosing ACS when the subject MIF and Nt-proBNP concentration is greater than a reference MIF and Nt-proBNP concentration, and
  performing percutaneous coronary intervention (PCI) and/or thrombolysis on the subject.

The present invention also provides a method for treating acute coronary syndrome (ACS) in a subject, the method comprising
  providing an individual who is determined to have a low likelihood of survival and/or high likelihood of non-fatal cardiac events by any method of the invention described herein,
  performing percutaneous coronary intervention (PCI) and/or thrombolysis on the subject,
  thereby treating the subject for ACS.

In any aspect of the invention, the method further comprises means for determining the concentration of troponin. Preferably, the concentration of MIF, Nt-proBNP and/or troponin are determined from plasma.

The present invention provides a device comprising means for determining concentration of macrophage migration inhibitory factor (MIF) and B-type natriuretic peptide (BNP) or N-terminal prohormone of brain natriuretic peptide (Nt-proBNP), in a sample from a subject, for use or when used in any method of the invention described herein.

In any aspect of the invention, the device further comprises means for determining the concentration of troponin. Preferably, the device is a point of care device. Preferably, the concentration of MIF, Nt-proBNP and/or troponin are determined from plasma.

In any aspect of the invention, concentration of MIF, Nt-proBNP and/or troponin may be determined by immunoassay.

In any aspect of the invention, there is provided a kit comprising a reagent for measuring macrophage migration inhibitory factor (MIF) and N-terminal prohormone of brain natriuretic peptide (Nt-proBNP) concentration in a sample from a subject, and/or comprising the device defined above. Preferably, the kit is for use in any method described herein.

In any aspect of the invention, there is provided a kit comprising a reagent for measuring macrophage migration inhibitory factor (MIF) and brain natriuretic peptide (BNP) concentration in a sample from a subject, and/or comprising the device defined above. Preferably, the kit is for use in any method described herein.

In any aspect of the invention, the kit further comprises means for determining the concentration of troponin. Preferably, the troponin is high sensitive-troponin T (hs-TnT). Preferably, the concentrations of MIF, Nt-proBNP (or BNP) and/or troponin are determined from plasma.

In any aspect of the invention, the means or reagent may comprise an anti-MIF antibody, an anti-Nt-proBNP (or BNP) antibody and/or and anti-troponin antibody.

In any aspect of the invention, there is provided a cardiac biomarker panel comprising plasma MIF and Nt-proBNP (or BNP) in a sample from a subject, wherein plasma MIF and Nt-proBNP (or BNP) concentration greater than a reference plasma MIF and Nt-proBNP (or BNP) concentration is prognostic of the magnitude of ACS in the subject. The cardiac biomarker panel may further comprise plasma troponin in a sample from a subject.

The present invention also provides use of a thrombolytic agent in the manufacture of a medicament for the treatment of ACS in a subject that has been determined to have a low likelihood of survival and/or high likelihood of non-fatal cardiac events by any method of the invention described herein.

The present invention also provides a thrombolytic agent for use in the treatment of ACS in a subject that has been determined to have a low likelihood of survival and/or high likelihood of non-fatal cardiac events by any method of the invention described herein.

The present invention also provides use of a means for detecting MIF, Nt-proBNP and/or troponin in the manufacture of a reagent or kit for use, or when used, in prognosing ACS. Preferably, prognosing ACS is by a method of the invention described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
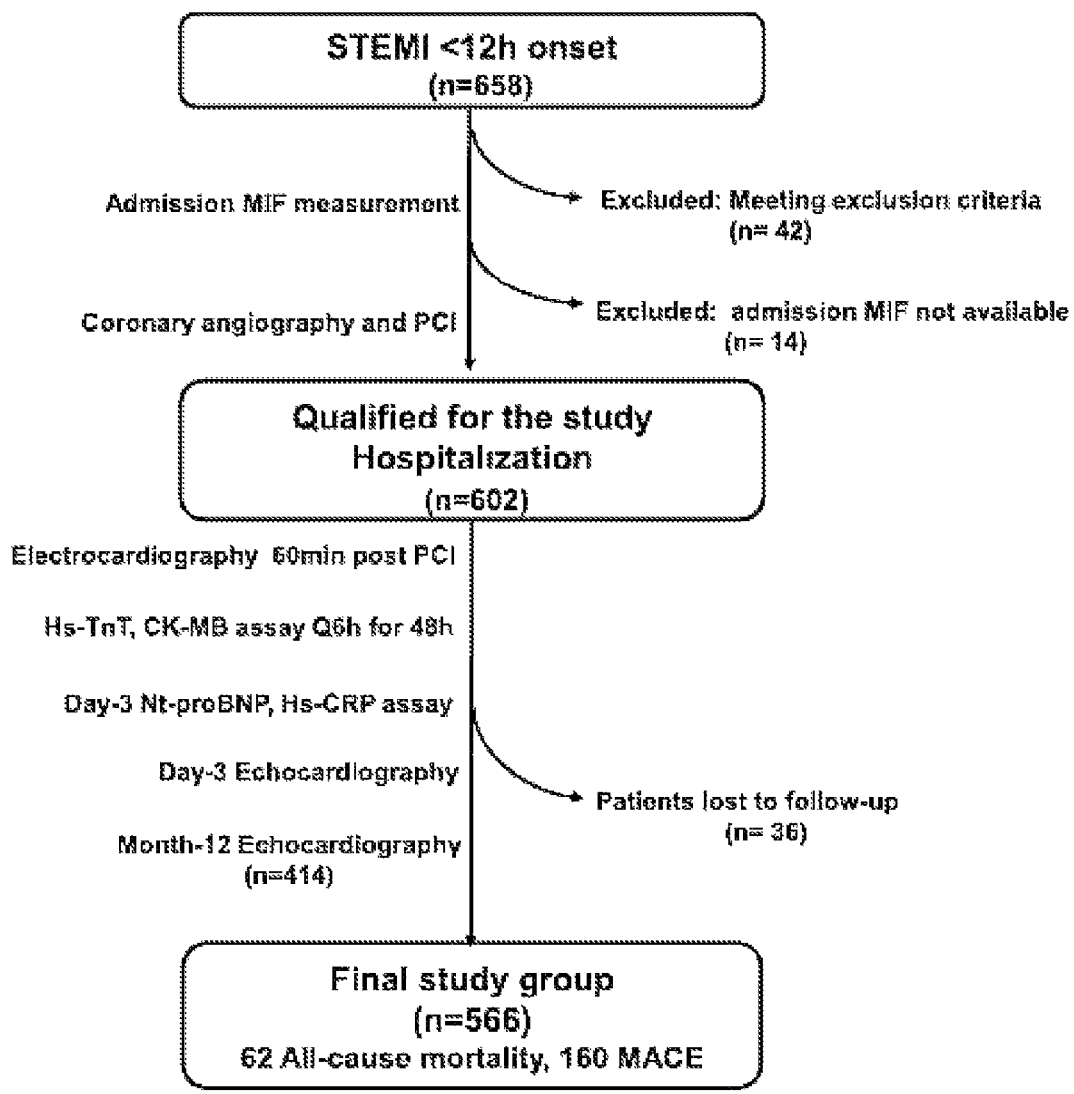
FIG. 1. Study flow chart. A total of 658 patients with confirmed diagnosis of STEMI were initially recruited into this prospective study. Of them, 42 patients were excluded based on exclusion criteria and another 50 patients were omitted due to lack of admission MIF measure (n=14) or lost during follow-up, leading to the final study cohort of 566 patients. Echocardiography was performed at day-3 and then at 12 months during follow-up period. Biochemical assays include MIF (admission), hs-TnT and CK-MB (within 48 hours), Nt-proBNP and Hs-CRP (both at day-3). CAG, coronary angiography; PPCI, primary percutaneous coronary intervention; hs-TnT, high sensitive troponin T; CK-MB, creatine kinase MB; Nt-proBNP, N-terminal prohormone of brain natriuretic peptide; CRP, C-reactive protein.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

Long-term mortality and morbidity following acute myocardial infarction (AMI) are largely determined by myocardial infarction (MI) size, and the extent of left ventricular (LV) dysfunction. Primary percutaneous coronary intervention (PCI) is now the established standard of treatment in patients with ST-elevation MI (STEMI) to limit infarct size and mortality. The inventors have surprisingly found that the determination of plasma concentration of MIF alone, or concentration of MIF and Nt-proBNP that are greater than normal (i.e. greater than a reference concentration) can prognose ACS, particularly STEMI, and can prognose survival and non-fatal cardiac events. The inventors have also advantageously found that the plasma concentrations of admission MIF, Nt-proBNP and troponin concentrations that are greater than normal (i.e. greater than a reference concentration) can prognose ACS, particularly STEMI, or prognose survival and non-fatal cardiac events.

Most subjects diagnosed with ACS such as AMI are treated by PCI. In hospitals lacking PCI facilities, either permanently or temporarily, the inventors propose that the determination of plasma concentration of admission MIF alone; MIF and Nt-proBNP; or MIF, Nt-proBNP and troponin that are greater than normal (i.e. greater than a reference concentration) can establish whether or not a given subject should be transferred to a hospital with PCI facilities. Moreover, the inventors have found that the above defined combinations have prognostic impact, and accordingly early accurate prediction of MI size in patients with AMI is advantageous, particularly in complex patients, or where local health-care resources are limited.

The inventors unexpectedly found that the above defined plasma biomarkers are prognostic for survival or non-fatal cardiac events. The inventors herein show that the measurement of MIF alone at certain concentrations; concentrations of MIF and Nt-proBNP; or MIF, Nt-proBNP and troponin is an accurate approach to aid prognosis of ACS. Concentrations of MIF and Nt-proBNP; or MIF, Nt-proBNP and troponin are more indicative of prognostic outcome when compared to MIF measurement alone. The inventors validated their findings and in certain aspects provide at least the following advantages:
(1) Higher plasma MIF concentration following diagnosis of ACS correlates with a more severe prognosis in the short and long term following diagnosis;
(2) Subjects who experience higher plasma MIF concentration following diagnosis of ACS are more likely to suffer from MACE, cardiac death, heart failure or death due to any cause;
(3) Higher plasma MIF and Nt-proBNP is associated with a higher risk of an event such as MACE or death and is a more accurate prognostic tool when compared to the individual components; and/or
(4) Higher plasma MIF, Nt-proBNP and troponin is associated with a higher risk of an event such as MACE or death and is a more accurate prognostic tool when compared to the individual components.

In other words, higher plasma concentrations of MIF and Nt-proBNP; or plasma MIF, Nt-proBNP and troponin can act as independent indicators of adverse outcomes of ACS. This approach may facilitate the identification of a high risk group that are likely to be associated with a poor prognosis following ACS. Those with higher levels of either plasma MIF and Nt-proBNP; or MIF, Nt-proBNP and troponin can be identified as having a poor prognosis following ACS. Elevated plasma concentrations of MIF and Nt-proBNP; or MIF, Nt-proBNP and troponin therefore have implications for prognosis and patient management.

The current invention provides the clinician or physician caring for a subject with information about the likelihood of non-fatal cardiac events and survival. On the basis of the results of the method of the invention, the clinician or physician can do, amongst other things, (i) enroll the patient in clinical trials for new therapies for ACS, (ii) treat the subject with alternative therapies, such as those which target the biomarkers, (iii) discuss the likely treatment and outcome scenarios with the subject, (iv) provide more regular or extensive post-treatment surveillance for a subject identified as having a low likelihood of survival and/or high likelihood of non-fatal cardiac event, and/or (v) proceed to treat a subject identified as high risk with added confidence the treatment is likely to provide benefit to the subject.

In any embodiment of the invention, the method may comprise a further treatment step such as PCI and/or thrombolysis. Thrombolysis and PCI can be critical in reducing morbidity and mortality in STEMI. Early knowledge of prognosis during the decision-making process about patient management provides numerous advantages. Firstly, clinicians assessing patients in whom the diagnosis of STEMI is not obvious or stuttering may benefit from the knowledge that an elevated biomarker is predictive of patient prognosis, which would facilitate the decision-making process about the timeliness of treatment, reperfusion, as well as post reperfusion supportive cardiac care required in coronary care unit or intensive care. Secondly, in regions where health-care resources are limited, early knowledge of prognosis may influence whether to transport the patient to a PCI-capable hospital, or trial thrombolysis first, especially in those with significant co-morbidities. When used in combination with Nt-proBNP, or alternatively with Nt-proBNP and troponin, MIF is useful in the clinical setting, especially in the emergency room setting as valuable prognostic indicators.

The present invention also provides for prognosis of impaired restoration of myocardial reperfusion and adverse improvement of LVEF. In particular, the present inventors have shown that MIF levels are an independent risk factor of impaired restoration of myocardial reperfusion. In those individuals that are identified as at risk of impaired restoration of myocardial reperfusion additional or more intensive intervention or monitoring can be undertaken. Further, in individuals where there is a risk of adverse or impaired improvement of recovery in LVEF then heart failure medication (e.g. ACE inhibitors, beta blockers etc) can be administered and heart failure preventative therapies can be applied.

Lastly, the information provided by the methods of the invention may be useful in clinical trial design whereby subjects that have an increased risk of a particular adverse outcome could be enrolled in a clinical trial. Post ACS therapeutic clinical trials of novel therapies are generally constrained by the requirement to use proven treatments thereby resulting in a low clinical end point event rate. This results in the need to use very large study cohorts in order to demonstrate, to a statistically significant level, further improvement due to the new agent. The ability to prospectively identify patients at higher risk of clinical events enables the use of smaller patient cohorts thereby resulting in potentially substantial cost savings. Furthermore patients unlikely to benefit are not exposed to an unproven agent. Thus, the methods disclosed herein could benefit the patient and also optimise a clinical trial by selecting those with a higher event rate thus reducing the number of participants.

The combination measurement of MIF and Nt-proBNP; or MIF, Nt-proBNP and troponin will therefore be highly valuable in the ongoing management, including the use of adjunctive therapy, and of patients post PPCI, as it provides further prognostic information on MI size, in addition to the advantages outlined above.

The person skilled in the art will appreciate that the magnitude of plasma MIF, Nt-proBNP and/or troponin concentrations may vary depending on the characteristics of the assay used to measure MIF, Nt-proBNP and/or troponin (e.g. different antibodies). Nevertheless, the person skilled in the art will also appreciate that, provided the appropriate control samples are analysed, the appropriate reference plasma MIF, Nt-proBNP and/or troponin concentrations can be determined.

The determination of levels of MIF, Nt-proBNP (or BNP) or troponin over a reference value (i.e., reference concentration) can be utilised to prognose ACS, particularly STEMI, or prognose survival and non-fatal cardiac events according to the methods described herein. Preferably, the reference concentration has been predetermined or is determined from a cohort of patients with known ACS (preferably ST-elevation myocardial infarction) outcome, preferably survival and non-fatal cardiac events as described herein.

In some aspects, the reference concentration stratifies the subject into one of two subgroups with the following rule: if the test or subject concentration is less than the reference concentration, then the subject is assigned to the group with an increased probability of survival and/or a decreased probability of non-fatal cardiac events; if the test or subject concentration is greater than or equal to the reference concentration, then the patient is assigned to the group with a decreased probability of survival or an increased probability of non-fatal cardiac events.

Alternatively, there may be multiple reference concentrations that stratify a subject into likelihood of low, moderate, or high likelihood of survival or non-fatal cardiac events.

The reference concentration may be selected according to any method known in the art. In particular embodiments, the reference concentration may be a predetermined value. Alternatively, the reference concentration may be determined during the course of the assay. For example, samples from known unaffected and/or affected subjects may be run concurrently with the test samples and a reference value determined therefrom. As a further alternative, test samples from a mixed population may be analyzed, and the reference value is determined based on the distribution of the results, e.g., using statistical methods as known in the art.

It is contemplated that over time, additional studies will generate new and additional information about the MIF, Nt-proBNP (or BNP) or troponin profiles for subjects suffering from ACS, particularly STEMI. The additional information may increase the accuracy, reliability, and confidence of the reference profiles, and accordingly increase the accuracy, reliability, and confidence of the determinations and recommendations realized by carrying out the methods. Thus, newly generated or revised reference concentrations and reference profiles may be used in accordance with the methods described herein. Thus, a person skilled in the art will appreciate that, reference concentrations may change over time, and provided that the appropriate control samples are analysed, the appropriate reference MIF, Nt-proBNP (or BNP) concentration can be determined.

A plasma MIF, Nt-proBNP (or BNP) or troponin concentration is greater than a reference plasma concentration when it exceeds the reference plasma MIF, Nt-proBNP (or BNP) or troponin concentration by 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 100% or more. A plasma MIF, Nt-proBNP (or BNP) or troponin concentration that exceeds the reference plasma MIF, Nt-proBNP (or BNP) or troponin concentration by 50% is equivalent to a 1.5-fold greater plasma MIF, Nt-proBNP (or BNP) or troponin concentration, and a plasma MIF, Nt-proBNP (or BNP) or troponin concentration that exceeds the reference plasma MIF, Nt-proBNP (or BNP) or troponin concentration by 100% is equivalent to a 2-fold greater plasma MIF, Nt-proBNP (or BNP) or troponin concentration, and so on. Accordingly, a plasma MIF, Nt-proBNP (or BNP) or troponin concentration is greater than a reference plasma MIF, Nt-proBNP (or BNP) or troponin concentration when it is 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold or more than the reference plasma MIF, Nt-proBNP (or BNP) or troponin concentration. In another embodiment, a plasma MIF, Nt-proBNP (or BNP) or troponin concentration is greater than a reference plasma MIF, Nt-proBNP (or BNP) or troponin concentration when it exceeds the reference plasma MIF, Nt-proBNP (or BNP) or troponin concentration and the difference is statistically significant as determined by methods known to the person skilled in the art. Alternatively, subjects that have MIF, Nt-proBNP (or BNP) or troponin values above about the $50^{th}$ percentile, $60^{th}$ percentile, $70^{th}$ percentile, $80^{th}$ percentile, $90^{th}$ percentile, $95^{th}$ percentile, $96^{th}$ percentile, $97^{th}$ percentile, $98^{th}$ percentile, 99th percentile, or higher, as compared with an appropriate matched control population may be identified as affected (ie having a moderate severity prognosis or a high severity (worst) prognosis).

A skilled person will understand that concentrations of about 40 ng/ml to 70 ng/ml MIF are associated with a moderate severity prognosis, concentrations higher than about 70 ng/ml MIF are associated with the worst prognosis, whilst concentrations less than about 40 ng/ml MIF are associated with the best prognosis. A subject with a MIF level greater than about 70 ng/ml is indicative of a prognosis of a 5 year MACE rate of about 35-40%, preferably about 40%, and a death rate of about 20%. In another aspect of the invention, concentrations of about 40 ng/ml to 73 ng/ml MIF are associated with a moderate severity prognosis, concentrations equal to or higher than about 73 ng/ml MIF are associated with the worst prognosis, whilst concentrations less than about 40 ng/ml MIF are associated with the best prognosis. In this aspect, a subject with a MIF level equal to or greater than about 73 ng/ml is indicative of a prognosis of a 5 year MACE rate of about 35-40%, preferably about 40%, and a death rate of about 20%.

A skilled person will understand that concentrations of troponin of about 2.5 ng/ml to about 4.5 ng/ml are associated with a moderate severity prognosis, concentrations higher than about 4.5 ng/ml are associated with the worst prognosis, whilst concentrations less than about 2.5 ng/ml are associated with better prognosis; with the best prognosis in combination with levels of MIF less than 40 ng/ml or levels of Nt-proBNP (or BNP) less than 700 pg/ml.

A subject with a troponin level greater than about 4.5 ng/ml in combination with MIF greater than about 70 ng/ml or 73 ng/ml and BNP greater than about 1200 pg/ml is indicative of a 5 year MACE prognosis rate of about 50% and death prognosis rate of about 25%.

A subject with a MIF level greater than about 70 ng/ml or 73 ng/ml and Nt-proBNP (or BNP) greater than about 1200 pg/ml is indicative of a 5 year MACE prognosis rate of about 50% and death prognosis rate of about 25%.

A skilled person will understand that concentrations of Nt-proBNP (or BNP) of about 700 pg/ml to about 1200 pg/ml are associated with a moderate severity prognosis, concentrations higher than about 1200 pg/ml are associated with the worst prognosis, whilst concentrations less than about 700 pg/ml are associated with better prognosis; with the best prognosis in combination with levels of MIF less than 40 ng/ml or levels of troponin less than 2.5 ng/ml.

Whilst MIF is an important early indicator of the prognosis of cardiovascular or acute myocardial ischaemic events, as shown herein, it is the combination of MIF and Nt-proBNP (or BNP); or MIF, Nt-proBNP (or BNP) and troponin that is the most clinically relevant measurement of prognosis of ACS, when compared to the individual components alone. Thus, in certain aspects present invention relates to a method for prognosing ACS, and a method for treating ACS by determining concentrations of MIF and Nt-proBNP (or BNP); or MIF, Nt-proBNP (or BNP) and troponin.

As used herein, a "method" for prognosing or treating ACS in a subject comprising determining plasma MIF and Nt-proBNP (or BNP); or MIF, Nt-proBNP (or BNP) and troponin concentration may be presented in an alternative form. In one example, the method may be in the form of "use" of plasma MIF concentration for diagnosing, prognosing or treating ACS in a subject. In a second example, the method may be in the form of plasma MIF concentration "for use" in prognosing or treating ACS in a subject. In another form, the method may be in the Swiss form "use of plasma MIF concentration in the manufacture" of a prognostic agent or a medicament.

In a preferred embodiment, the method of prognosis of ACS in a subject is performed in vitro on a plasma (or serum or blood) sample. In other words, any method of the invention may be an in vitro method. For example, a step of determining, measuring or analysing in any method of the invention described herein is performed in vitro.

In one embodiment, the methods of the invention do not comprise a step of taking a sample from the subject.

Subsequent to prognosis of ACS in the subject, the method may further comprise treating the subject by percutaneous coronary intervention (PCI) and/or thrombolysis.

The currently recommended treatment for STEMI is primary PCI (ie PCI delivered as soon as possible after diagnosis) if this is available and can be delivered in a timely fashion. PCI Involves the placement in the femoral, radial (or occasionally) brachial artery of a catheter with a lumen which is then introduced, under X ray imaging, into the coronary artery containing the stenosis/thrombosis responsible for the STEMI. The narrowing is then expanded with a fluid filled balloon. In some cases this is followed by the placement of a stent (a cylindrical metal scaffold) at the site of the region which has been dilated. The stent may or may not be impregnated with a drug to prevent recurrence of narrowing (this depends on clinical circumstances and angiographic findings). If primary PCI cannot be performed then the STEMI patient is usually treated with a fibrinolytic agent to dissolve the clot present at the culprit site. The fibrinolytic agent is delivered by peripheral venous cannulation. In some cases there are residual symptoms or physical signs persisting (or recurring) despite fibrinolytic treatment and in these cases the patient may undergo subsequent "rescue" PCI.

Treatment may further comprise administration of an agent that can dissolve a thrombus. Such an agent may be referred to as thrombolytic. Examples of thrombolytic agents are urokinase, recombinant tissue plasminogen activator (TPA), prourokinase, anisoylated purified streptokinase activator complex (APSAC) and streptokinase. Treatment may further comprise administration of an agent that can prevent or reduce new thrombus or rethrombosis. Such an agent may be referred to as anti-thrombotic. Examples of anti-thrombotic agents may be an anti-platelet drug, for example, a glycoprotein IIB/IIIA inhibitor (e.g. abciximab, eptifibatide, or tirofiban), or an adenosine diphosphate (ADP) receptor inhibitor (e.g. clopidogrel, prasugrel, ticagrelor, or ticlopidine).

As used herein, performing thrombolysis includes administering any one or more thrombolytic agents as described herein.

Preferably, the sample from which MIF, Nt-proBNP (or BNP) and troponin is measured is plasma. Plasma may be obtained by anti-coagulating blood with EDTA, sodium heparin, lithium heparin, sodium citrate or sodium oxalate. Alternatively, the sample in which MIF, Nt-proBNP (or BNP) and troponin is measured from is serum or blood. In one embodiment, the sample may be whole blood.

"Acute coronary syndrome" or "ACS" refers to a spectrum of conditions involving chest discomfort or other symptoms caused by lack of oxygen to the heart. The symptom is consequent upon erosion, fissuring or rupture of a pre-existing atherosclerotic plaque, and occurs spontaneously. In the absence of evidence of myocardial necrosis, unstable angina is diagnosed, but in the presence of evidence of myocardial necrosis (e.g. a plasma biomarker), AMI is diagnosed. Thus, ACS may comprise unstable angina or AMI. "ACS" does not include stable angina.

Patients with ACS display a variety of physical symptoms. These include constricting chest pain that often radiates to the neck, jaw, shoulders, or down the inside of the left or both arms and can have accompanying symptoms of dyspnea, diaphoresis, palpitations, light-headedness, and nausea. Patients experiencing ACS present to the physician with clinical symptoms including unstable angina, non-ST-elevation non-Q wave myocardial infarction ("NST"-"MI"), ST-elevation non-Q wave MI, and transmural (Q-wave) MI.

"Acute myocardial infarction" or "AMI" refers to the interruption of blood supply to a part of the heart, causing restriction in blood supply ("ischaemia"), lack of oxygen, and cell death ("necrosis"), and is a type of ACS. This may result in damage or death of heart muscle tissue (myocardium). Thus, "myocardial necrosis" refers to the death of heart cells. AMI may be divided into ST elevation myocardial infarction (STEMI), diagnosed by elevation of the ST segment of the electrocardiogram, and non-ST elevation myocardial infarction (non-STEMI), diagnosed by absence of such electrocardiographic changes. STEMI may be treated with thrombolysis or PCI. Non-STEMI may be managed with medication, although PCI is often performed during hospital admission.

As used herein, the term MACE ('major adverse cardiac events) refers to cardiac death and other non-fatal cardiovascular outcomes. Non-exhaustive examples of MACE include myocardial infarction, unstable angina, heart failure, percutaneous cardiac intervention, coronary artery bypass grafting, malignant dysrhythmia, cardiac shock, implantable cardiac defibrillator, and malignant dysrhythmia.

As used herein, the term "HF-rehospitalisation free survival" refers to the prognosis of those patients not readmitted to hospital due to heart failure, following diagnosis of ACS. In other words, re-hospitalisation for HF can be defined as a hospital readmission for which HF was the primary reason.

As used herein, the term "all-cause mortality free survival" refers to prognosis of those patients who have not died from any underlying condition.

As used herein, the term "cardiac death free survival" refers to prognosis of those patients who have not died from any cardiac related condition.

In any aspect of the invention, prognosis may be indicative of survival or non-fatal cardiac events 1, 2, 4, 6, 8, 10, 12, 14, 16, 18, 20, 22, 24, 26, 28, 30, 32, 34, 36, 28, 40, 42, 44, 46, 48, 50, 52, 54, 56, 58, 60, 62, 64, 66, 68, 70, 72, 74, 76, 78, 80 or more, months following diagnosis of ACS.

A "coronary event" refers to any severe or acute cardiovascular condition including AMI, unstable angina, or cardiac mortality.

"Left ventricular hypertrophy" or "LVH" refers to thickening of the myocardium (muscle) of the left ventricle of the heart.

"Left ventricular end-diastolic volume" or "LVEDV" is defined as the volume of blood within the left ventricle immediately before contraction.

"Left ventricular end-systolic volume" or "LVESV" is defined as the volume of blood remaining within the left ventricle at the end of contraction.

"Stroke volume" is defined as the difference between LVEDV and LVESV and refers to the volume of blood ejected from the left ventricle with each contraction (heartbeat).

"Left ventricular ejection fraction" or "LVEF" is defined as the fraction of the LVEDV that is ejected with each contraction (heartbeat); that is, "stroke volume" divided by LVEDV. LVEF may be expressed as a percentage.

As used herein, "infarct size" is measured by cardiac magnetic resonance (CMR), integrated biomarker levels or echocardiography and is defined as the area of hyperenhanced myocardium (bounded by manually traced endocardial and epicardial contours) on each short axis slice multiplied by the slice thickness and the myocardial density of 1.05 g/ml to obtain the infarct mass, and expressed as a percentage of left ventricular mass.

As used herein, "left ventricular mass indexed" refers to the left ventricular mass in g divided by the square of the height in m of a subject, and is expressed in units $g/m^2$.

As used herein, "biomarker" refers to a measurable substance, detection of which typically indicates a particular cardiac disease. A "biomarker" may indicate a change in expression or state of the measurable substance that correlates with the prognosis of a disease. A "biomarker" may be a protein or peptide. A "biomarker" may be measured in a bodily fluid such as plasma, blood or serum. As used herein, "biomarkers" include plasma macrophage migration inhibitory factor (MIF), Nt-proBNP, B-type natriuretic peptide (BNP) and troponin, and may further include myoglobin, C reactive protein or creatine kinase (CK).

In one embodiment, MIF, Nt-proBNP (or BNP) and troponin are full length. In another embodiment, MIF, BNP and troponin comprise a fragment thereof. Preferably, the MIF, Nt-proBNP (or BNP) and troponin are human.

Troponin may be troponin I, including cardiac troponin I (cTnl), troponin T or high sensitivity troponin T (hs-TnT). A skilled person will understand that hs-TnT is a form of troponin that allows for very low concentrations of troponin to be measured accurately and early following ACS.

Preferably, MIF is human MIF for clinical prognosis and comprises the amino acid sequence provided as NCBI Reference Sequence: NP 002406.1 (SEQ ID NO: 1):

MPMFIVNTNVPRASVPDGFLSELTQQLAQATGKPPQYIAVHVVPDQLMAF

GGSSEPCALCSLHSIGKIGGQNRSYSKLLCGLLAERLRISPDRVYINYYD

MNAANVGWNNSTFA

Alternatively, MIF may be from another mammal, for example primate, murine, bovine, ovine, equine, porcine, canine or feline, for veterinarian prognosis.

As used herein, "prognosis" and related terms refer to the description of the likely outcome of ACS. This may include risk of MACE, MACE-free survival, HF-rehospitalisation free survival, all-cause mortality free survival and cardiac death free survival. Prognosis may also include prediction of favorable responses to ACS treatments, such as thrombolysis. As measurement of plasma biomarker concentration correlates with the magnitude of AMI (e.g. quantification of infarct size), plasma concentration of the biomarkers defined above enables assessment of the likely morbidity and mortality arising from the infarct (prognosis). As will be understood by those skilled in the art, the prediction may need not be correct for 100% of the subjects evaluated. The term, however, requires that a statistically significant portion of subjects can be identified as having an increased probability of having a given outcome.

Furthermore, measurement of plasma MIF, BNP and/or troponin concentration may quantify the ACS, thereby enabling prognosis of the ACS.

As used herein, "onset of symptoms" or "symptom onset" is the time at which a subject begins to experience a departure from normal physiology.

As used herein, "admission" refers to the formal acceptance by a hospital or other health care facility of a subject who is to be provided with medical treatment. In particular, "admission" will be associated with an accurate time at which the subject is accepted for medical treatment.

As used herein, admission MIF, preferably plasma MIF, concentration refers to the MIF concentration measured in a sample (preferably concentration measured in plasma derived from a blood sample) obtained as soon as practicable after admission, but typically less than 4 hours after symptom onset. Alternatively, admission plasma MIF concentration may refer to the MIF concentration measured in plasma derived from a blood sample obtained 210 minutes, 180 minutes, 150 minutes, 120 minutes, 110 minutes, 100 minutes, 90 minutes, 80 minutes, 70 minutes, 60 minutes, 50 minutes, 40 minutes, 30 minutes, 20 minutes, 10 minutes or 5 minutes or less after symptom onset.

If a subject has not been accepted for medical treatment, but is at home or place of work for example, admission plasma MIF concentration is understood to mean less than 240 minutes, or 210 minutes, 180 minutes, 150 minutes, 120 minutes, 110 minutes, 100 minutes, 90 minutes, 80 minutes, 70 minutes, 60 minutes, 50 minutes, 40 minutes, 30 minutes, 20 minutes, 10 minutes or 5 minutes or less after symptom onset.

As used herein, Nt-proBNP (or BNP), preferably plasma Nt-proBNP (or BNP), concentration refers to the Nt-proBNP (or BNP) concentration measured in a sample obtained from a patient following symptom onset or hospital admission, preferably the concentration measured in plasma derived from a blood sample. In particular, the sample may be plasma derived from a blood sample obtained less than about, or between, any of the following: about 0.5 days, 1.0 day, 1.5 days, 2.0 days, 2.5 days, 3.0 days, 3.5 days, 4.0 days, 4.5 days, 5.0 days, 5.5 days, 6.0 days, 6.5 days or more after symptom onset. Preferably Nt-proBNP (or BNP) concentrations are determined in plasma derived from a blood sample obtained from a patient 3 days following symptom onset or hospital admission.

As used herein, troponin, preferably plasma troponin, concentration refers to the troponin measured in a sample obtained from a patient following symptom onset or hospital admission, preferably the concentration measured in plasma derived from a blood sample. In particular, the sample may be plasma derived from a blood sample obtained less than about, or between, any of the following: about 0.5 days, 1.0 day, 1.5 days, 2.0 days, 2.5 days, 3.0 days, 3.5 days, 4.0 days, 4.5 days, 5.0 days, 5.5 days, 6.0 days, 6.5 days, 7.0 days, 7.5 days, 8.0 days, 8.5 days, 9.0 days, 9.5 days, 10.0 days, 10.5 days, 11 days, 11.5 days, 12 days or more after symptom onset or hospital admission.

The time at which a sample may be taken from a subject is applicable to all aspects of the invention.

As used herein, "means for measuring" plasma MIF, Nt-proBNP (or BNP) or troponin refers to any mechanism by which MIF, Nt-proBNP (or BNP) or troponin can be determined (assayed or quantified) and may include any molecule or reagent that is capable or directly or indirectly binding MIF, Nt-proBNP (or BNP) or troponin. For instance, plasma MIF, Nt-proBNP (or BNP) or troponin may be determined in a sample using any method known to those skilled in the art for detecting proteins including, but not limited to, for example immunoassays such as, for example ELISA, enzyme immunoassay (EIA), Western blot, slot blot, dot blot, or immunoprecipitation followed by sodium dodecyl sulfate polyacrylamide gel electrophoresis, (SDS-PAGE), chromatography and the like. Dendrimer-enhanced radial partition immunoassays and immunofluorescence assays, for example, are known in the art and are commercially available. Troponin may also be measured using a highly sensitive troponin assay.

As used herein, "assay", and variants thereof, refers to measurement or quantification of the concentration of plasma MIF, Nt-proBNP (or BNP) or troponin or other biomarkers herein defined.

The terms "antibody" and "antibodies" refer to monoclonal antibodies, polyclonal antibodies, bi-specific antibodies, multispecific antibodies, grafted antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Depending on the amino acid sequence of the constant domain of their heavy chains, immunoglobulins can be assigned to different classes. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known. Immunoglobulin molecules are of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. The terms "antibody" and "immunoglobulin" are used interchangeably in the broadest sense. In some embodiments an antibody is part of a larger molecule, formed by covalent or non-covalent association of the antibody with one or more other proteins or peptides.

The terms "binding fragment," "functional fragment," "antibody fragment" or "antigen binding fragment" are used herein, for purposes of the specification and claims, to mean a portion or fragment of an intact antibody molecule, preferably wherein the fragment retains antigen-binding function. Examples of antibody fragments include Fab, Fab', $F(ab')_2$, Fd ($V_H$ and $C_{H1}$ domains), Fd' and Fv (the $V_L$ and $V_H$ domains of a single arm of an antibody) fragments, diabodies, linear antibodies, variable light chains (VL), variable heavy chains (VH), single-chain antibody molecules, single-chain binding polypeptides, scFv, scFv2 (a tandem linkage of two scFv molecules head to tail in a chain), bivalent scFv, tetravalent scFv, one-half antibodies, dAb fragments, variable NAR domains, and bispecific or multispecific antibodies formed from antibody fragments (e.g., a bi-specific $Fab_2$, and a tri-specific $Fab_3$, etc.).

Methods for generating antibodies are known in the art and/or described in Harlow and Lane (editors) Antibodies: A Laboratory Manual, Cold Spring Harbor Laboratory, (1988). Generally, in such methods an antigen or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, subcutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present invention. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies, for example, which do not express murine antibodies, can also be used to generate an antibody of the present invention (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison WI 53713, USA) is used to produce cell lines secreting MAbs (e.g., as described in Largaespada et al, *J. Immunol. Methods.* 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

Any antibody used in accordance with the present invention may be a synthetic antibody. For example, the antibody is a chimeric antibody, a humanized antibody, a human antibody synhumanized antibody, primatized antibody or a de-immunized antibody.

One exemplary agent for detecting a protein of interest is an antibody, or antigen binding fragment thereof, capable of specifically binding to plasma MIF, Nt-proBNP (or BNP) or troponin. The antibody may detectably labelled, either directly or indirectly.

Anti-MIF antibodies or antigen binding fragments thereof are commercially available from suppliers such as Abcam and include: chicken polyclonal anti-MIF antibody (ab34644); goat polyclonal anti-MIF antibody (ab36146, ab14574); rabbit polyclonal anti-MIF (C-terminus) antibody (ab65869); rabbit polyclonal anti-MIF antibody (ab86670); mouse monoclonal anti-MIF antibody (ab55445); and mouse anti-MIF monoclonal antibody [2Ar3] (ab14575).

Troponin and anti-hsTnT antibodies are commercially available from suppliers such as Roche (07007302190) and Abcam (ab47003 or EP1106Y). Approaches to measure hs-TnT include fragment antigen binding of two hs-TnT specific monoclonal antibodies, detectable in a sandwich format. Antibodies recognise epitopes corresponding to amino acids 125-131 and 135-147 of hs-TnT. Detection can be performed by chemiluminesence using Tris (bipyridol)-ruthenium (II).

Anti-Nt-proBNP (or BNP) antibodies are available from commercial suppliers including Abcam (15F11 or 5B6) and ThermoFischer Scientific (MA1-20631). Polyclonal antibodies bind to epitopes on residues 1-21 and 29-50 and expression can be detected through routine means in the art including labelling with biotin followed by ruthenium. The complex binds nTproBNP which is detected through streptavidin labelled microparticles.

Immunoassays for plasma MIF, Nt-proBNP (or BNP) or troponin may comprise incubating a sample with a detectably labelled antibody, or antibody fragment, capable of specifically binding plasma MIF, Nt-proBNP (or BNP) or troponin, and detecting the bound antibody by any of a number of techniques well-known in the art. As discussed in more detail, below, the term "labelled" can refer to direct labelling of the antibody via, e.g., coupling (i.e., physically linking) a detectable substance to the antibody, and can also refer to indirect labelling of the antibody by reactivity with another reagent that is directly labelled. An example of indirect labelling includes detection of a primary antibody using a fluorescently labelled secondary antibody.

The sample can be brought in contact with and immobilised on a solid support or carrier, or other solid support, which is capable of immobilising soluble proteins. The support can then be washed with suitable buffers followed by treatment with the detectably labelled antibody. The solid support can then be washed with the buffer a second time to remove unbound antibody. The amount of bound label on solid support can then be detected by conventional methods.

By "solid support or carrier" is intended to be any support capable of binding an antigen or an antibody. Well-known supports or carriers include nitrocellulose, glass, polystyrene, polypropylene, polyethylene, dextran, nylon, amylases, natural and modified celluloses, polyacrylamides and magnetite. The nature of the solid support or carrier can be either soluble to some extent or insoluble.

The solid support can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Those skilled in the art will know many other suitable carriers for binding antibody or antigen, or will be able to ascertain the same by use of routine experimentation.

One of the ways in which an antibody specific for plasma MIF, Nt-proBNP (or BNP) or troponin can be detectably labelled is by linking the antibody to an enzyme for use in an enzyme immunoassay. The enzyme bound to the antibody will react with an appropriate substrate, preferably a chromogenic substrate, in such a manner as to produce a chemical moiety which can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection and measurement can be accomplished by colorimetric methods which employ a chromogenic substrate for the enzyme. Detection and measurement can also be accomplished by visual comparison of the extent of enzymatic reaction of a substrate in comparison with similarly prepared standards.

Detection and measurement can also be accomplished using any of a variety of other immunoassays. For example, by radioactively labelling the antibody or functional antibody fragment, it is possible to detect plasma levels of biomarkers through the use of a radioimmunoassay (RIA). The radioactive isotope (e.g., $^{125}$I, $^{131}$I $^{35}$S, $^{32}$P or $^{3}$H) can be detected by such means as the use of a gamma counter or a scintillation counter or by autoradiography.

It is also possible to label the antibody with a fluorescent or luminescent compound. When the fluorescently labelled antibody is exposed to light of the appropriate wavelength, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labelled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Fluorescence energy transfer compounds may also be employed.

The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester. Likewise, a bioluminescent compound can be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

In another embodiment, specific binding molecules other than antibodies, such as aptamers, may be used to bind plasma MIF, Nt-proBNP (or BNP) or troponin.

Other "means for measuring" plasma MIF, Nt-proBNP (or BNP) or troponin include chromatography or electrophoresis with dye-based detection, or proteomics approaches employing spectrometry such as mass spectrometry.

Spectrometry may be used to measure dye-based assays, including visible dyes, and fluorescent or luminescent agents.

A protein chip assay may be used to measure plasma MIF, Nt-proBNP (or BNP) or troponin.

Plasma MIF, Nt-proBNP (or BNP) or troponin can also be measured or assayed using of one or more of the following methods. For example, methods may include nuclear magnetic resonance (NMR) spectroscopy, a mass spectrometry method, such as electrospray ionization mass spectrometry (ESI-MS), ESI-MS/MS, ESI-MS/(MS)n (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS)3 quadrupole time-of-flight (Q-TOF), atmospheric pressure chemical ionization mass spectrometry (APCI-MS), APCI-MS/MS, APCI-(MS), atmospheric pressure photoionization mass spectrometry (APPI-MS), APPI-MS/MS, and APPI-(MS). Other mass spectrometry methods may include quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof.

In one embodiment, LDI-TOF-MS allows the generation of large amounts of information in a relatively short period of time. A biological sample is applied to one of several varieties of a support that binds MIF, BNP or troponin in the sample. Samples are applied directly to these surfaces in volumes as small as 0.5 pL, with or without prior purification or fractionation. The sample can be concentrated or diluted prior to application onto the support surface. Laser desorption/ionization is then used to generate mass spectra of the sample in as little as three hours.

A bead assay may also be used to measure plasma MIF, Nt-proBNP (or BNP) or troponin concentrations.

As used herein, "device" refers to a physical arrangement of components for performing an assay for measuring plasma MIF, Nt-proBNP (or BNP) or troponin. The device may be a point-of-care device used by a medical practitioner to measure plasma MIF, Nt-proBNP (or BNP) or troponin without the need for laboratory measurement. Alternatively, a point-of-care device may be used domestically, for example in a subject at risk of a first or subsequent coronary event. Alternatively, the device may be in a laboratory located separately to the subject in whom plasma MIF, Nt-proBNP (or BNP) or troponin is to be measured.

The device may employ an electrochemical cell. Electrochemical cells may use electrodes positioned within the cell in a side-by-side or "coplanar" layout to minimize the electrical interference between the electrodes. Alternatively, electrochemical cells may use non coplanar electrodes that exploit the electrical interference between the electrodes to yield additional information about the sample including information that can correct for patient to patient variations in hematocrit and interfering chemical substances that may be present in a sample.

The device may provide a qualitative output (e.g. yes/no, presence/absence/, high/low), a numerical or quantified output (e.g. concentration), or an output for visual inspection (e.g. a colour for comparison with a reference scale).

As used herein, "kit" refers to a physical arrangement of components, one of which may be the device for measuring plasma MIF, Nt-proBNP (or BNP) and/or troponin. The kit may include a reagent such as an anti-MIF, anti-Nt-proBNP (or BNP) or anti-troponin immunogenic moiety, a secondary detection agent for detecting the immunogenic moiety, or a reagent for sample preparation and/or processing, for example a buffer. The kit may include means, such as reagents, to perform a highly sensitive assay, such as for the detection of hs-TnT.

The device or kit may be accompanied by instructions or directions for use of the device or kit in any method described herein.

As used herein, a device or kit may be in alternative forms. One form designates either suitability for or restriction to a specific use and is indicated by the word "for". Another form is restricted to a specific use only and is indicated by the words "when used for" or similar. In one embodiment of the method for treating ACS in a subject, plasma MIF, Nt-proBNP (or BNP) or troponin is measured using the device disclosed herein.

Figure 3:
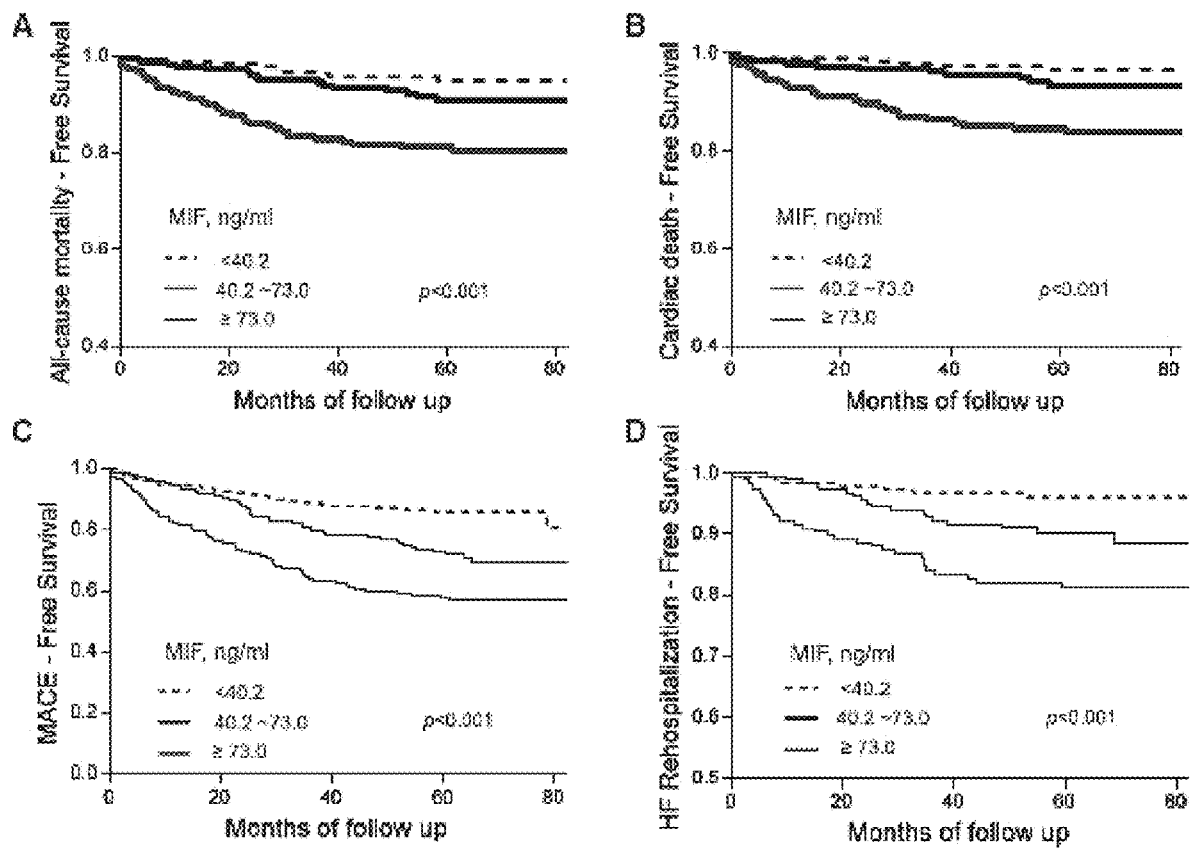
FIG. 3. All-cause death, cardiovascular death, HF re-hospitalisation and MACE according to tertiles of admission MIF concentrations. Kaplan-Meier event-free survival curves for (A) All-cause death, (B) Cardiovascular death, (C) Mace and (D) HF re-hospitalisation admission in STEMI patients according to tertile MIF. Patients of high tertile MIF levels (red line, 73.0 ng/ml; n=188) were compared with those of median tertile (black line, 40.2-73.0 ng/ml; n=189) and low tertile (black dotted line, <40.2 ng/ml; n=189).
Figure 5:
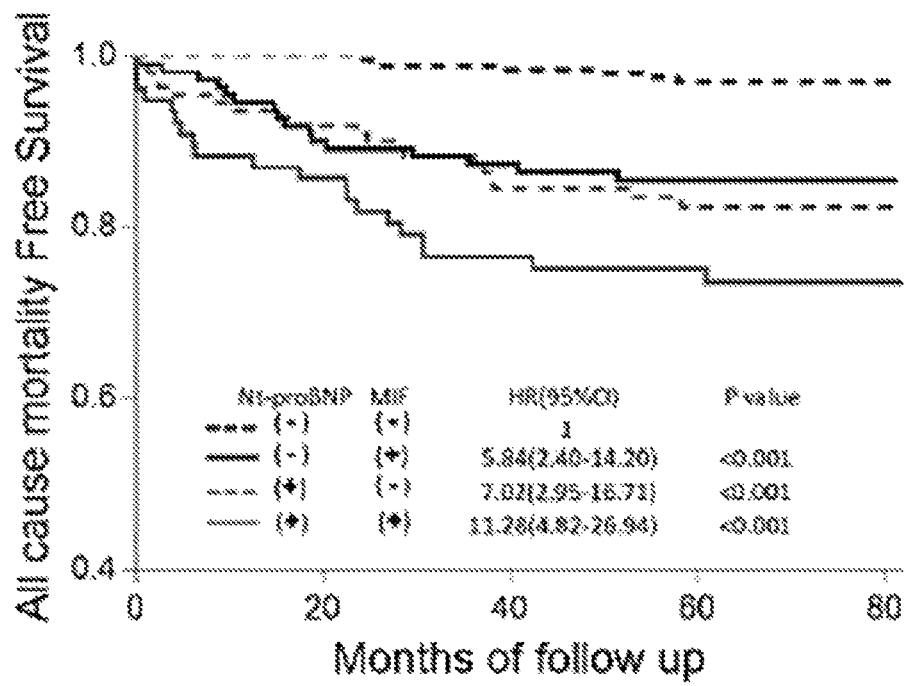
FIG. 5. All-cause mortality and MACE in patients according to whether MIF, Nt-proBNP and/or hs-TnT in high tertiles. Comparison of all-cause mortality and major adverse cardiovascular events in ST-elevation myocardial infarction patients based on macrophage migration inhibitory factor (MIF) and Nt-proBNP tertiles. The Kaplan-Meier event-free survival curves for (A) all-cause mortality and (B) major adverse cardiovascular events (MACE) in patients based on migration inhibitory factor and Nt-proBNP levels. Patients were divided into tertile groups separately and defined as positive (+) group with high tertile, negative group with median or low tertile level. Four groups came into being as NtproBNP(+) MIF(+) (red line, n=77), Nt-proBNP(−) MIF(+) (black line, n=111), Nt-proBNP(+) MIF(−) (dotted red line, n=111) and Nt-proBNP(−) MIF(−) (dotted black line, n=267). P-values in inserts indicate difference vs. the Nt-proBNP(−) MIF(−) group.
Figure 5:
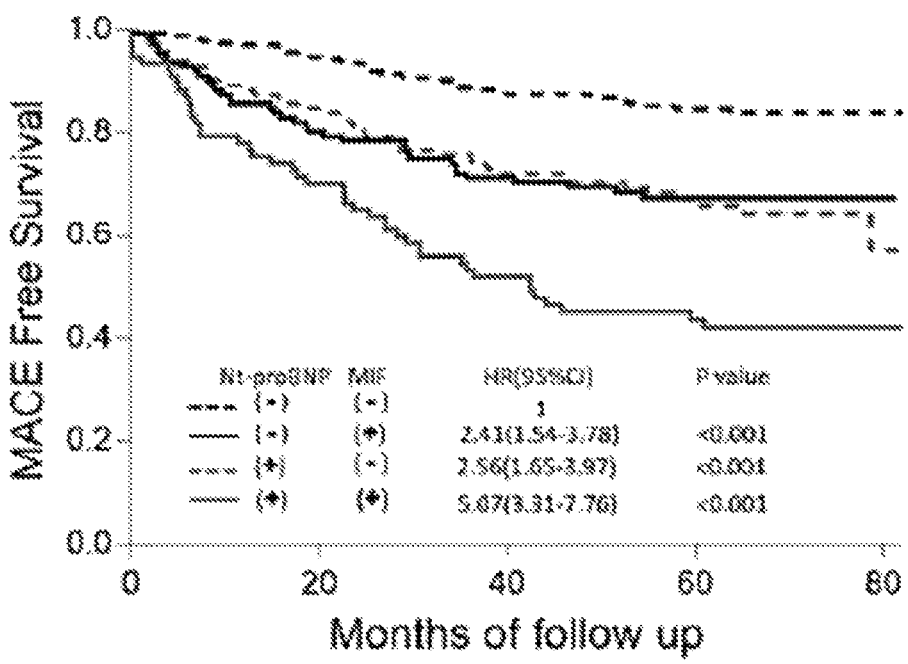

Survival analysis can be performed using the Kaplan-Meier method (as described in the Example herein and shown in FIGS. 3 and 5). The Kaplan-Meier method estimates the survival function from life-time data. In medical research, it can be used to measure the fraction of patients living for a certain amount of time after treatment. A plot of the Kaplan-Meier method of the survival function is a series of horizontal steps of declining magnitude which, when a large enough sample is taken, approaches the true survival function for that population. The value of the survival function between successive distinct sampled observations ("clicks") is assumed to be constant.

An important advantage of the Kaplan-Meier curve is that the method can take into account "censored" data-losses from the sample before the final outcome is observed (for instance, if a patient withdraws from a study). On the plot, small vertical tick-marks indicate losses, where patient data has been censored. When no truncation or censoring occurs, the Kaplan-Meier curve is equivalent to the empirical distribution.

In statistics, the log-rank test (also known as the Mantel-Cox test) is a hypothesis test to compare the survival distributions of two groups of patients. It is a nonparametric test and appropriate to use when the data are right censored. It is widely used in clinical trials to establish the efficacy of new drugs compared to a control group when the measurement is the time to event. The log-rank test statistic compares estimates of the hazard functions of the two groups at each observed event time. It is constructed by computing the observed and expected number of events in one of the groups at each observed event time and then adding these to obtain an overall summary across all time points where there is an event. The log-rank statistic can be derived as the score test for the Cox proportional hazards model comparing two groups. It is therefore asymptotically equivalent to the likelihood ratio test statistic based from that model.

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

Example 1

This study was conducted to determine whether a single measurement of admission MIF alone or in combination with BNP and/or troponin, could provide predictive information of long-term survival and nonfatal cardiovascular events in patients with STEMI.
Methods
Study Population and Design The inventors consecutively recruited during June 2010 to April 2015 patients with STEMI who received treatment with PCI at the Department of Cardiology, Third Hospital of Peking University. Inclusion criteria were: (1) presentation with STEMI (typical symptoms for >30 minutes and <12 hours plus persistent ST-segment elevation of 2 mV in at least two contiguous precordial ECG-leads or mV in at least two contiguous limb ECG-leads or a newly developed left bundle branch Block); (2) with invasive treatment by PCI; (3) availability of MIF measurements from blood samples on admission. Patients having one or more of the following criteria were excluded: (1) previous ACS within 1 month; (2) rescue angioplasty; (3) current infections, known malignant, inflammatory or autoimmune disease; (4) end-stage renal disease (estimated Glomerular Filtration Rate <30 ml/min/kg) and (5) unwillingness. The process of recruitment and study protocol are illustrated in FIG. 1.

Baseline clinical data such as history of disease and medication were collected from medical records. Hypertension was diagnosed in the presence of active treatment with antihypertensive agents or otherwise as a systolic blood pressure of 140 mmHg and/or diastolic blood pressure of 90 mmHg on at least 2 separate occasions. Hypercholesterolemia was diagnosed in the presence of active treatment with lipid-lowering drugs or value of total cholesterol 6.22 mmol/L or low density lipoprotein cholesterol 4.14 mmol/L. Current smokers were defined as those currently smoking any tobacco. Diagnosis of diabetes mellitus was confirmed by the active treatment with antidiabetic medicine or with a fasting plasma glucose level 7 mmol/L or a nonfasting level of 11.1 mmol/L. Patients were prospectively classified according to maximum Killip class by 3 clinicians on admission and during hospitalisation. This prospective cohort study was approved by the Human Ethics Committee, Peking University Health Science Centre and performed in accordance with the requirements of the Declaration of Helsinki. Informed consent was obtained from all participants.
PPCI and Medication After a previous loading dose of 300 mg aspirin and 600 mg clopidogrel, coronary angiogram was performed. Quantitative coronary angiographic analysis was performed on analysis before and after interventions. Culprit lesion, numbers of significantly stenosed vessels, TIMI reclassification pre- and post-PCI were recorded. Interventions were performed according to current guidelines. Thrombus aspiration, use of Glycoprotein IIb/IIIa inhibitors (Tirofiban), intra-aortic balloon pump (IABP) implanting were administered at the discretion of the operator. There were two independent observers blinded to our trial calculating ST-segment resolution by predefined criteria at 60 min after revascularization with a cutoff value <50% defined as incomplete ST-segment resolution.

Following the PCI procedure, patients were prescribed Enoxaparin Sodium (100 U/kg/q12h for 3 days), and other secondary preventions as aspirin (100 mg/day), clopidogrel (75 mg/day for 12 months), cholesterol-lowering treatment (statins), β-receptor antagonists and Angiotensin-Converting Enzyme Inhibitors or angiotensin receptor blocker (ACEI/ARB). All patients received standard and individualized medical treatment and management at the discretion of an attending cardiologist.
Study End Points and Follow Up The short-term endpoint of our study was incomplete ST-segment resolution post primary PCI as a surrogate of inefficient myocardial reperfusion. Long-term following up was accomplished by reviewing the hospital records, contacting patients or their relatives by telephone individually. Information was collected on occurrence of death due to cardiovascular causes (CVD), major adverse cardiac events (MACE) consisting of all-cause mortality, recurrent MI, and re-hospitalisation for heart failure (HF). The long-term end points were all-cause mortality and the composite endpoint of MACE. Recurrent MI was defined as accordance with the universal definition proposed in 2012. Re-hospitalisation for HF was defined as a hospital readmission due to HF as the primary reason.
Echocardiography Echocardiography was performed at day-3 and around 12 months of follow-up period after MI using Vivid 7 (Vingmed, GE, Horten, Norway) with a 3.3-MHz multiphase array probe. Standard echocardiographic views were acquired under supervision of experienced cardiologists. Left ventricular end-diastolic dimension and ejection fraction (LVEF) was obtained using the modified biplane Simpson method.
Routine Laboratory Measurements Venous blood samples were collected at admission and then every 6 hours for the first two days for assay of CK-MB and Hs-TnT. Peak concentrations were identified to estimate infarct size. Nt-proBNP and hs-CRP concentrations were determined on median day 3 post-MI, since their prognostic value at this time outperformed those of other timings during the acute phase.

All routine biochemical assays were performed immediately after collection of blood samples using commercially available automated platform. CK-MB, hs-CRP, blood lipids and plasma creatinine concentration were analyzed using an AU5400 automatic chemical analyzer (Beckman Coulter, California, USA). Both of Hs-TnT and NT-pro-BNP were measured using E601 immunoassay analyzer (Roche Diagnostics, Mannheim, Germany). Estimated glomerular filtration rate (eGFR) was calculated according to Cockcroft-Gault formula. All the results of tests were obtained at the Clinical Biochemistry Department of Beijing University Third Hospital based on manufacturers' recommendation or literature.
Measurement of Plasma MIF Concentration Immediately after admission, blood samples were collected prior to antiplatelet drugs and primary PCI by venepuncture into vacutainer tubes containing heparin lithium. Plasma was isolated from whole blood by centrifugation at 3000 rpm for 10 min at 4° C., then divided into aliquots and stored at −80° C. until analysis. Repeated freeze-thaw cycles were avoided. Plasma MIF was measured, in duplicates, using Quantikine MIF ELISA kits (DMFOOB, R&D Systems) according to manufacturer's specifications. The coefficient of variation for intra- and inter-assay variation was 2.8±1.6% and 5.8±1.3% respectively. For comparison, we also measured MIF level of healthy people (n=65) and of patients presenting to the emergency department with chest pain not to be due to cardiac ischemia (n=600). All these assays were performed by personnel blinded to patient's identity and outcome.

Statistical Analysis

Aorta was primarily analysed by identifying 3 tertiles of initial MIF measurement. Categorical variables were summarized as percentage and compared using chi-squared test to compare between tertile MIF groups. Continuous variables are presented as means±SD or median with interquartile range (IQR) and the association between tertile MIF with them were tested by one-way ANOVA or Kruskal-Wallis rank-sum test. The association between MIF level and other continuous variables (e.g. biomarkers, LVEF) was tested by Spearman's rank order correlation. Due to non-normal distribution, all biomarkers were logarithmically or log-2 transformed prior to entry into the statistical models. The primary endpoint (complete ST-segment resolution) was analyzed with a logistic regression model.

Kaplan-Meier curves were generated to visualize the relationship of tertile MIF level with long-term prognosis. Univariate and multivariate analyses were performed using the Cox proportional hazard models. Four models for the adjustment of covariates were utilized: Model 1, adjusted for age, sex, eGFR and log 2MIF; Model 2, adjusted for all factors in model 1 plus other characteristics as body BMI, haemoglobin, previous MI, diabetes mellitus, hypertension, current smoking, hypocholesteremia, symptom-admission time <6 h, 3 vessel disease, Killip class>1, culprit lesion of left anterior descending (LAD), ST-segment resolution, thrombus aspiration, use of Glycoprotein IIb/IIIa inhibitor during the PCI, TIMI reclassification pre- and post-PCI; Model 3, adjusted for all factors in Model 2 plus conventional biomarkers including hs-TnT peak, Nt-proBNP and hs-CRP; Model-4, adjusted for all factors in Model 3 plus day-3 LVEF.

Patients were defined separately with individual biomarker in high tertile as positive group (+), while in median and low tertile as negative group (−) to study prognostic value of different combinations including Nt-proBNP/MIF, hs-TnT peak/MIF, Nt-proBNP/hs-TnT peak and Triple groups. Discrimination was evaluated using C-statistic. Continuous net reclassification improvement (NRI) and integrated discrimination improvement (IDI) were also calculated to quantify the degree of correct reclassification as a result of adding admission MIF to the clinical risk models. All probability values are two-tailed and was considered statistically significant <0.05. Calculations of C-statistics, NRI and IDI were performed using package "surviC1" and "survIDINRI" in R programming 3.4.0 for Windows (R Development Core Team, 2016), other data analyses were performed using SPSS (version 22.0; SPSS, Inc. Chicago, IL).

Results

Clinical Characteristics

Figure 6:
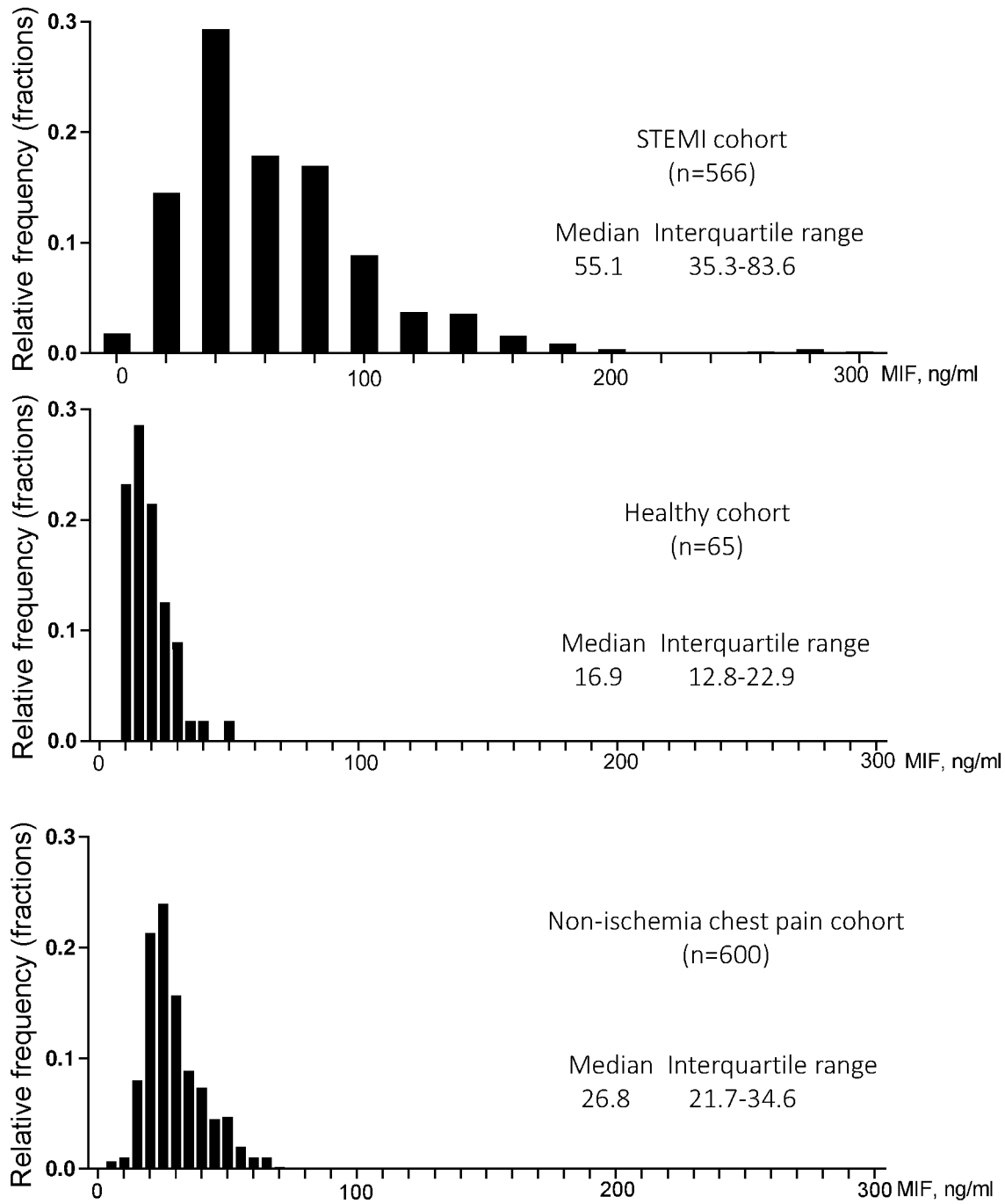
FIG. 6. Frequency distributions of MIF in STEM patients, healthy subjects and non-ischemia chest pain patients. Non-ischemia chest pain patients were patients presenting chest pain to emergency department finally without evidence of cardiac ischemia, infection, malignancy by following up through medical records or direct telephone contact with patients.

A total of 658 patients with confirmed diagnosis of STEMI were initially recruited into this prospective study. Of them, 56 patients were excluded based on exclusion criteria and another 36 patients were lost to follow-up whilst 14 patients did not have available blood samples or lacked admission MIF measures, leading to the final study cohort of 566 patients (FIG. 1). Their median age was 61 years and 79.9% were male. The median (interquartile range) of admission MIF was 55.1 (35.3-83.6) ng/ml, significantly higher than other two reference groups: healthy control 16.9 (12.8-22.9) ng/ml and chest pain patients presented at emergency department without ischaemic etiology 26.8 (21.7-34.6) ng/ml (FIG. 6).

The clinical characteristics of this patient cohort are summarized according to MIF tertile in Tables 1 and Table 2. MIF levels were not associated with neither age, gender or eGFR, BMI, nor diastolic blood pressure or heart rate. STEMI patients in the high MIF tertile group tended to have a higher prevalence of hypertension (P=0.029), and were more likely to have culprit vessel lesion in the LAD (P=0.001). Other conditions of previous risk factors of coronary heart diseases and CAG results were similar in three groups (Table 1). There was also no significant difference between the 3 groups in the proportion of patients treated with secondary prevention of aspirin, clopidogrel, statins, ACEI or ARBs, and β-blockers, on admission (not shown) or at discharge (Table 1) between the 3 groups.

Moderate but highly significant correlations were observed between concentrations of admission MIF and necrosis markers, peak levels of hsTnT (r=0.486, P<0.001) and CK-MB (r=0.343, P<0.001). Meanwhile, MIF level was also associated with inflammatory markers such as white blood cell count (r=0.210, P<0.001), nonfasting glucose (r=0.126, P<0.006) at initial presentation and CRP at Day 3 (r=0.154, P<0.001), while not with hemoglobin, serum cholesterol or HbA1c %.

TABLE 1

Characteristics of basic clinical data of patients with STEMI

| | | Tertiles of admission MIF (ng/ml) | | | |
|---|---|---|---|---|---|
| | Total | <40.2 (Low) | 40.2~73.0 (Median) | ≥73.0 (High) | P value |
| number | 566 | 189 | 189 | 188 | |
| Age | 60.1 ± 13.0 | 61.1 ± 12.0 | 60.2 ± 13.3 | 61.9 ± 13.5 | 0.448 |
| Male gender, % (n) | 80 (452) | 75 (142) | 84 (159) | 80 (151) | 0.091 |
| Systolic BP (mmHg) | 131 ± 21 | 131 ± 19 | 129 ± 19 | 133 ± 24 | 0.132 |
| Diastolic BP (mmHg) | 77 ± 15 | 79 ± 14 | 76 ± 14 | 77 ± 16 | 0.122 |
| Heart rate (bpm) | 75 ± 15 | 73 ± 13 | 77 ± 16 | 75 ± 15 | 0.054 |
| Body mass index (kg/M$^2$) | 25.6 ± 3.3 | 25.6 ± 4.4 | 25.4 ± 2.6 | 25.8 ± 2.5 | 0.504 |
| eGFR (mmol/L) | 89 ± 26 | 87 ± 24 | 88 ± 24 | 92 ± 29 | 0.165 |
| Admission time <3 h (%) | 43.8 (248) | 42.3 (80) | 42.3 (80) | 46.8 (88) | 0.599 |
| History, % (n) | | | | | |
| Hypertension | 57.6 (326) | 54.0 (102) | 53.4 (101) | 65.4 (123) | 0.029 |
| Diabetes | 24.6 (139) | 27.0 (51) | 25.9 (49) | 20.7 (39) | 0.322 |
| Hypercholesteremia | 31.8 (180) | 32.3 (61) | 30.2 (57) | 33.0 (62) | 0.829 |
| Smoking | 67.3 (381) | 65.1 (123) | 68.8 (130) | 68.1 (128) | 0.717 |
| Previous MI | 6.9 (39) | 10.1 (19) | 6.9 (13) | 3.7 (7) | 0.053 |

TABLE 1-continued

Characteristics of basic clinical data of patients with STEMI

| | Total | Tertiles of admission MIF (ng/ml) | | | P value |
| | | <40.2 (Low) | 40.2~73.0 (Median) | ≥73.0 (High) | |
|---|---|---|---|---|---|
| Angiographic data, % (n) | | | | | |
| Culprit vessel LAD | 46.1 (261) | 46.0 (87) | 36.5 (69) | 55.9 (105) | 0.001 |
| 3-vessel lesion | 37.5 (212) | 34.4 (65) | 41.3 (78) | 36.7 (69) | 0.372 |
| Stents | 97.3 (551) | 96.3 (182) | 97.8 (185) | 97.8 (184) | 0543 |
| Thrombus aspiration | 16.2 (92) | 16.4 (31) | 18.0 (34) | 14.4 (27) | 0.633 |
| Tirofiban | 32.9 (186) | 36.5 (69) | 32.8 (62) | 29.3 (55) | 0.325 |
| IABP in situ | 3.4 (19) | 2.1 (4) | 3.7 (7) | 4.3 (8) | 0.488 |
| TIMI = 0, before PCI | 78.1 (442) | 81.0 (153) | 81.0 (153) | 72.3 (136) | 0.066 |
| TIMI <3, After PCI | 4.2 (24) | 3.2 (6) | 3.2 (6) | 6.4 (12) | 0.123 |
| ST-segment resolution <50% | 26.7 (151) | 14.3 (27) | 22.8 (43) | 43.1 (81) | <0.001 |
| LVEDD >55 mm (male), >50 mm (female) | 16.4 (92) | 14.4 (27) | 10.6 (20) | 24.3 (45) | 0.001 |
| LVEF <50% | 36.4 (204) | 23.0 (43) | 29.8 (56) | 56.8 (105) | <0.001 |
| Killip class II-IV | 18.0 (102) | 11.1 (21) | 19.6 (37) | 23.4 (44) | 0.006 |
| Medication, % (n) | | | | | |
| Clopidogrel | 98.9 (560) | 98.4 (186) | 99.5 (188) | 98.9 (186) | 0.604 |
| Aspirin | 98.4 (557) | 98.9 (187) | 97.4 (184) | 98.9 (186) | 0.597 |
| Statins | 95.8 (542) | 96.8 (183) | 95.2 (180) | 95.2 (179) | 0.672 |
| ACEI/ARBs | 73.5 (416) | 76.2 (144) | 70.4 (133) | 73.9 (139) | 0.434 |
| β-blocker | 72.8 (412) | 76.7 (145) | 70.9 (134) | 70.7 (133) | 0.331 |

Data are presented either as mean±SD, percentage or median (25th percentile; 75th percentile). Categorical variables are indicated as percentage (%) of patients. eGFR: estimated glomerular filtration rate. LAD, left anterior descending; IABP, intra-aortic balloon pump; LDL, low-density lipoprotein; LVEF, left ventricular ejection fraction; LVEDD, left ventricular end-diastolic diameter; PCI, Percutaneous coronary intervention. P-values were derived from Mann-Whitney U statistics, One-way ANOVA test, or Chi-squire test for comparison among MIF tertile groups.

TABLE 2

Baseline laboratory measurements

| | Total | Tertiles of admission MIF (ng/ml) | | | P value |
| | | <40.2 (Low) | 40.2~73.0 (Median) | ≥73.0 (High) | |
|---|---|---|---|---|---|
| number | 566 | 189 | 189 | 188 | |
| White blood cells (10$^9$/L) | 10.2 ± 3.3 | 9.4 ± 3.0 | 9.9 ± 3.0 | 11.2 ± 3.7 | <0.001 |
| Hemoglobin (g/L) | 143 ± 21 | 141 ± 21 | 143 ± 18 | 144 ± 23 | 0.171 |
| Platelets (10$^9$/L) | 218 ± 48 | 214 ± 41 | 217 ± 51 | 224 ± 52 | 0.099 |
| Non-fasting blood glucose (mmol/L) | 6.3 (5.1-7.5) | 6.0 (5.1-7.8) | 6.5 (5.1-7.5) | 6.7 (5.5-8.1) | 0.024 |
| HbA1c(%) | 6.3 ± 1.3 | 6.2 ± 1.2 | 6.4 ± 1.4 | 6.3 ± 1.4 | 0.294 |
| peak CK-MB (U/L) | 195 (111-317) | 161 (69-260) | 213 (85-317) | 275 (199-407) | <0.001 |
| peak Hs-TnT (ng/ml) | 4.6 (2.3-6.3) | 2.8 (1.5-4.1) | 4.5 (2.2-6.2) | 6.3 (4.2-7.9) | <0.001 |
| Nt-proBNP (pg/ml) | 976 (433-2219) | 718 (258-1897) | 747 (395-1735) | 1284 (625-3130) | 0.002 |
| Hs-CPR (pg/ml) | 6.60 (3.60-12.16) | 4.71 (2.02-12.81) | 6.15 (2.79-17.85) | 8.08 (3.20-16.32) | 0.007 |
| LDL-c (mmol/L) | 2.89 ± 1.12 | 2.92 ± 0.89 | 2.86 ± 0.91 | 2.89 ± 1.46 | 0.893 |

Data are mean±SD, percentage or median (25th percentile; 75th percentile). NT-proBNP, indicates N-terminal prohormone of brain natriuretic peptide; LDL-c, low-density lipoprotein-cholesterol; HDL-c, high-density lipoprotein-cholesterol; CK-MB, Creatine kinase MB fraction; CRP, C-reactive protein; hs-TnT, high sensitive-troponin T. P-values were derived from Mann-Whitney U test or One-way ANOVA for comparison among MIF tertile groups.

Admission MIF and Cardiac Function at Acute and 12-Month Phase.

Figure 2:
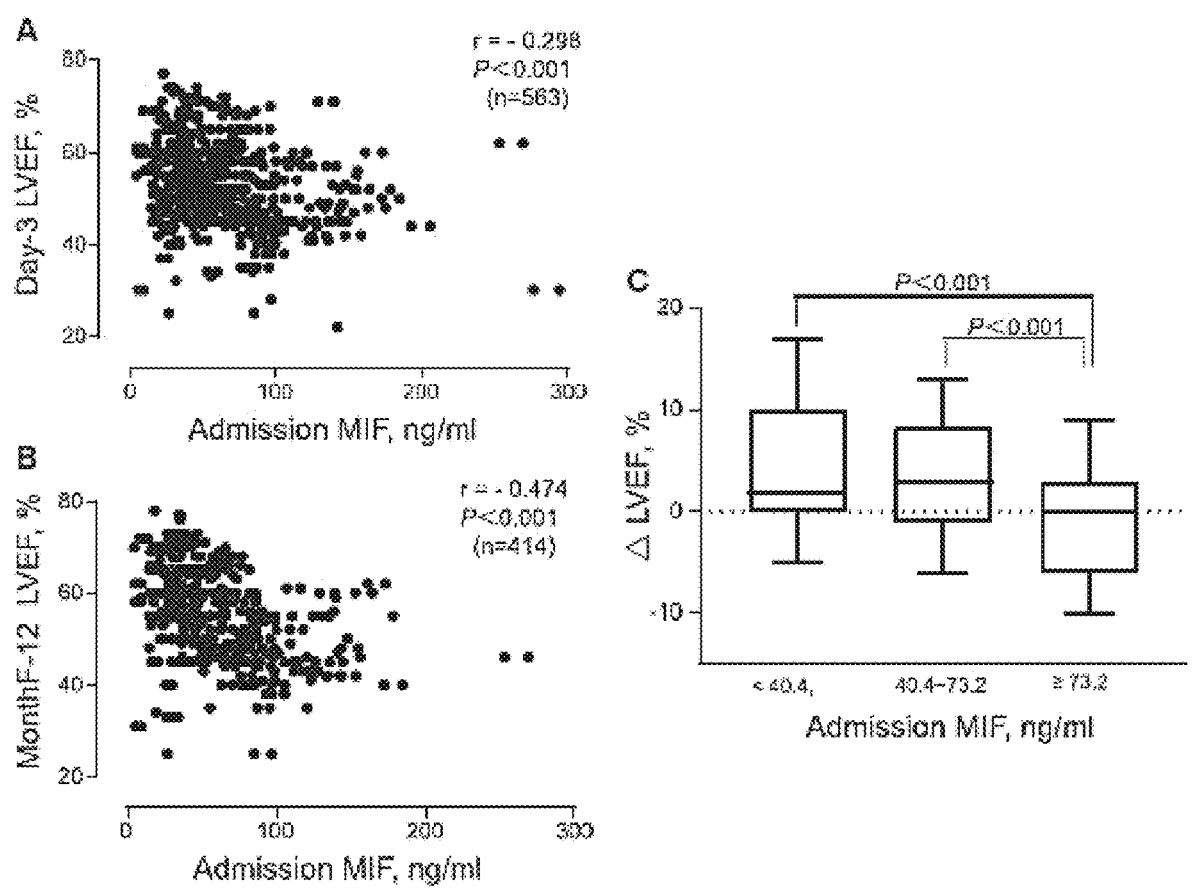
FIG. 2. Admission MIF correlated with 3-day/12-month LVEF and improvement. (A-B) Admission MIF was negatively correlated with LVEF by echocardiography performed on day-3 and 12 months (F12) post STEMI. (C) Patients were divided into three groups according to migration inhibitory factor tertiles. After calculating differences of LVEF (ΔLVEF) of the two time-points, patients with high tertile MIF failed to improve LVEF relative to other two tertile groups (P<0.001).

Patients in the high tertile admission MIF group had a higher proportion of maximum Killip class >1 during hospitalisation in comparison with those with low tertile (23.4% vs. 11.1%, p=0.006). Admission MIF level was associated with elevated Nt-proBNP levels (r=0.190, P<0.001), impaired LVEF [r=−0.298, 95% CI (−0.382,−0.215), P<0.001] and enlarged LVDD (r=0.115, <0.006) on Day-3 after MI. Repeated echocardiography was performed at 12 months during follow-up and MIF had a stronger correlation with F12 LVEF[r=−0.474, 95% CI (−0.550,−0.384), P<0.001] and LVDD (r=−0.261, P<0.001, n=414). Importantly, after calculating changes in LVEF, our data revealed that high tertile MIF was associated with lack of improvement of LVEF % (P<0.001) at 12-month post-MI compared with the 3 day value (FIG. 2).

MIF and Incomplete ST-Segment Resolution

In the subgroup of high tertile MIF patients, the incidence of ST-segment resolution <50% at 60 mins post-PCI was 3.3 and 1.9-fold higher than that of the low- or median-tertile groups (p<0.001, Table 1). In contrast, admission hs-TnT, CK-MB were not associated with incomplete ST-segment resolution (P=0.263 & P=0.486). In multivariable logistics analyses, as log-2 transformed continuous variables, admission MIF was an independent predictor for incomplete resolution of ST-segment elevation with odds ratio (OR) 1.72 (95% CI 1.35-2.18; P<0.001) per doubling in MIF concentration after adjustment of age, gender, eGFR, symptom to admission time<6 h, infarct location, previous history of diabetes, current smoking and WBC levels at initial presentation. Another remaining-significant predictor was anterior infarction location was with OR of 2.02 (95% CI 1.35-3.01; P=0.001).

MIF and Long-Term Adverse Outcomes

During a median follow-up period of 64 months (ranging from 0.03 to 83 months), there were 160 patients who had MACE. Of them, 62 patients died with 46 due to cardiovascular causes. There were 56 patients re-admitted due to HF, and 42 experienced recurrent MI. The admission MIF level was found to be closely associated with long-term adverse outcomes. As shown in FIG. 3, Kaplan-Meier survival curves and log-rank analyses demonstrated different incidence distributions, according to MIF tertiles, of all-cause mortality, cardiovascular death, HF re-hospitalisation and MACE (all P<0.001). To explore the independency of MIF in prognostic prediction, we applied univariate and multi-variate Cox-regression analyses using different models (Table 3). In all 4 clinical risk models tested including clinical characteristics and conventional biomarkers such as Nt-ptoBNP, peak hs-TnT, hs-CRP, and Day-3 LVEF, MIF remained as an independent predictor of all-cause mortality, cardiovascular death and MACE.

TABLE 3

Multivariable Cox Regression Analyses for admission MIF in All-Cause Mortality, Cardiovascular death, HF re-hospitalisation and MACE

|  |  | MACE | All-cause mortality | Cardiovascular death | HF re-hospitalization |
|---|---|---|---|---|---|
| Unadjusted | HR (95% CI) | 1.91 (1.57-2.31) | 2.49 (1.80-3.44) | 2.86 (1.95-4.20) | 2.00 (1.43-2.79) |
|  | P value | <0.001 | <0.001 | <0.001 | <0.001 |
| Model 1 | HR (95% CI) | 1.71 (1.40-2.08) | 2.54 (1.81-3.55) | 2.88 (1.92-4.32) | 1.97 (1.36-2.77) |
|  | P value | <0.001 | <0.001 | <0.001 | <0.001 |
| Model 2 | HR (95% CI) | 1.68 (1.38-2.05) | 2.47 (1.78-3.42) | 2.60 (1.74-3.87) | 1.93 (1.38-2.69) |
|  | P value | <0.001 | <0.001 | <0.001 | <0.001 |
| Model 3 | HR (95% CI) | 1.46 (1.10-1.95) | 2.37 (1.70-3.31) | 2.55 (1.53-4.26) | 1.84 (1.30-2.60) |
|  | P value | 0.009 | 0.001 | 0.001 | 0.001 |
| Model 4 | HR (95% CI) | 1.39 (1.12-1.71) | 2.27 (1.42-3.22) | 2.49 (1.52-4.24) | 1.58 (1.13-2.24) |
|  | P value | 0.002 | 0.010 | 0.004 | 0.008 |

Model 1: adjusted for age, sex, eGFR and log2MIF;
Model 2: model 1 plus other characteristics as body mass index (BMI), hemoglobin, previous MI, diabetes mellitus, hypertension, current smoking, hypocholesteremia, symptom-admission time <6 h, 3 vessel disease, Killip class >1, culprit lesion of LAD, ST-segment resolution, use of Glycoprotein IIb/IIIa inhibitor(Tirofiban) during the PCI, Timi class pre and post PPCI;
Model 3: model 2 plus logNt-proBNP, logTnT peak and loghs-CRP;
Model 4: model 3 plus LVEF.

We used a clinical risk model consisting of the followings: age, sex, eGFR, hemoglobin, previous MI, diabetes mellitus, hypertension, current smoking, symptom-admission time <6 h, culprit lesion of LAD, 3 vessel disease, Killip class >1, culprit lesion of LAD, ST-segment resolution, TIMI class pre- and post-PCI, hs-TnT peak and day-3 LVEF. Our data showed that inclusion of MIF significantly improved predictive ability estimated by C-statistics of total death [0.84 (0.77-0.91) vs. 0.89 (0.83-0.94), P=0.020] and MACE [0.72 (0.67-0.77) vs. 0.74 (0.70-0.79), P=0.047]. Meanwhile, we calculated how many patients were re-classified after the addition of continuous log 2MIF using continuous NRI 0.34 (95% CI: 0.04-0.47) for all-cause mortality and 0.24 (95% CI: 0.11-0.34) for MACE. Calculated IDI yielded similar improvement with 0.06 (95% CI: 0.00-0.144) for all-cause mortality and 0.05 (95% CI: 0.01-0.09) for MACE (Table 4).

TABLE 4

Discrimination and Reclassification Performance of the Addition of admission MIF Concentrations in Predicting end points, based on C-Statistics, continuous NRI and IDI

|  | All-cause mortality | | | MACE | | |
|---|---|---|---|---|---|---|
| log2 MIF | Clinical model | Clinical model + MIF | P | Clinical model | Clinical model + MIF | P |
| C statistics (95% CI) | 0.84 (0.77-0.91) | 0.89 (0.83-0.94) | 0.02 | 0.72 (0.67-0.77) | 0.74 (0.70-0.79) | 0.047 |
| Continuous | Reference | 0.34 | 0.02 | Reference | 0.24 | <0.001 |

TABLE 4-continued

Discrimination and Reclassification Performance of the Addition
of admission MIF Concentrations in Predicting end points,
based on C-Statistics, continuous NRI and IDI

| log2 MIF | All-cause mortality | | | MACE | | |
|---|---|---|---|---|---|---|
| | Clinical model | Clinical model + MIF | P | Clinical model | Clinical model + MIF | P |
| NRI (95% CI) | | (0.04-0.47) | | | (0.70-0.79) | |
| IDI (95% CI) | Reference | 0.06 (0.00-0.14) | 0.04 | Reference | 0.05 (0.02-0.09) | <0.001 |

Clinical Model: Age, sex, eGFR, BMI, hemoglobin, previous MI, diabetes mellitus, hypertension, current smoking, hypocholesteremia, symptom-admission time <6 h, 3 vessel disease, Killip class >1, culprit lesion of LAD, ST-segment resolution, use of Glycoprotein IIb/IIIa inhibitor(Tirofiban) during the PCI, Timi class pre and post PPCI, hs-TnT peak and LVEF. NRI, net reclassification index; IDI, integrated discrimination improvement.

Combined Prognostic Value of MIF and Nt-proBNP

The prognostic merit of MIF relative to hs-TnT peak, CRP, and Nt-proBNP was compared by C-statistics. We found that MIF(C statistics: 0.71, 95% CI: 0.64-0.78) provided better prognostic information than peak hs-TnI (C statistics: 0.63, 95% CI: 0.56-0.71, P<0.03) and hs-CRP (C statistics: 0.53, 95% CI: 0.46-0.60, P<0.001), but was comparable to Nt-proBNP (C statistics: 0.70, 95% CI: 0.62-0.75, P=0.33) in all-cause mortality. Cox regression analysis revealed that, after adjustment for Model 3 (including MIF and golden standard biomarkers as Nt-proBNP, peak hs-TnT and hs-CRP), only admission MIF and Nt-proBNP were independent predictors for adverse outcomes of STEMI patients. However, after adjustment for Model 4 with addition of day-3 LVEF, Nt-proBNP remains significant only for cardiovascular death (Table 5).

TABLE 5

Multivariable Cox Regression Analyses for day 3 Nt-proBNP in All-Cause
Mortality, Cardiovascular death, HF re-hospitalisation and MACE

| log Nt-proBNP | | MACE | All-cause mortality | CVD | HF re-hospitalisation |
|---|---|---|---|---|---|
| unadjusted | HR(95% CI) | 2.65 (1.97-3.57) | 3.66 (2.26-5.91) | 4.84 (2.42-9.66) | 4.53 (2.71-7.58) |
| | P value | <0.001 | <0.001 | <0.001 | <0.001 |
| model 1 | HR(95% CI) | 2.33 (1.71-3.20) | 2.53 (1.54-4.16) | 3.39 (1.60-7.21) | 3.65 (1.91-6.97) |
| | P value | <0.001 | <0.001 | 0.003 | <0.001 |
| model 2 | HR(95% CI) | 1.99 (1.45-2.73) | 2.15 (1.30-3.60) | 3.12 (1.35-7.18) | 3.08 (1.82-5.22) |
| | P value | <0.001 | 0.004 | 0.008 | <0.001 |
| model 3 | HR(95% CI) | 1.73 (1.26-2.38) | 2.28 (1.32-3.95) | 3.10 (1.35-7.18) | 2.89 (1.47-5.67) |
| | P value | 0.001 | 0.003 | 0.008 | 0.002 |
| model 4 | HR(95% CI) | 1.34 (0.96-1.89) | 1.56 (0.87-2.80) | 2.64 (1.15-5.99) | 2.12(1.18-3.80) |
| | P value | 0.089 | 0.139 | 0.022 | 0.012 |

Model 1: adjusted for age, sex, eGFR and logNt-proBNP;
Model 2: model 1 plus other characteristics as body mass index (BMI), hemoglobin, previous MI, diabetes mellitus, hypertension, current smoking, hypocholesteremia, symptom-admission time <6 h, 3 vessel disease, Killip class >1, culprit lesion of LAD, ST-segment resolution, use of Glycoprotein IIb/IIIa inhibitor(Tirofiban) during the PCI, TIMI class pre and post PPCI;
Model 3: model 2 plus log2MIF. logTnT peak and loghs-CRP;
Model 4: model 3 plus LVEF.

Figure 4:
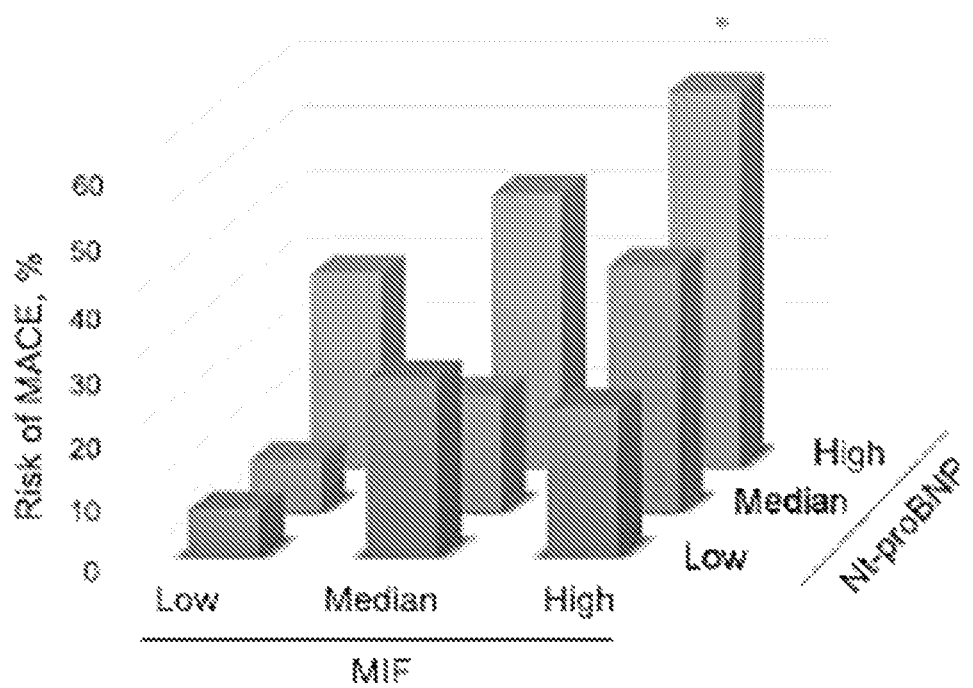
FIG. 4. Risk stratification of MACE in STEMI patients according to tertiles of plasma MIF and NT-proBNP concentrations. Combination of admission MIF and Nt-proBNP (day-3) identified sub-groups of patients with increased risk of MACE during the follow-up period. Patients were separately divided into tertile groups based on MIF and Nt-proBNP levels. The risk of MACE significantly increased in patients with both biomarkers in high tertile compared with patients with both biomarkers in the low tertile (*P<0.001).

To investigate additive prognostic value of combination of MIF and Nt-proBNP, risk stratification of STEMI patients for the endpoints was made according to tertiles of MIF and NT-proBNP levels. The risk of the all-cause mortality (26% vs 0.0%, P<0.001) and MACE (57.1% vs 7.4%, P<0.001; FIG. 4) increased significantly in patients with both biomarkers in the highest tertile compared with other counterparts with both biomarkers in the low tertile. Furthermore, to study prognostic value of different combinations, STEMI patients were divided into two subgroups with positive group (+) if individual biomarkers in high tertile and as negative group (−) if in median or low tertile.

Compared with those in both negative group, the hazard ratio of patients in Nt-proBNP (+) MIF (+) group was over 11-fold in total mortality [hazard ratio (HR) 11.28; 95% CI 4.82-26.94; P<0.001, FIG. 5], similar to that of Triple (+) groups (HR 11.39; 95% CI 4.29-29.68; P<0.001). However, the hazard ratio of patients in peak hs-TnT(+) MIF(+) or Nt-proBNP(+) peak hs-TnT(+) group was 4.12 (95% CI 2.16-7.85) or 6.60 (95% CI 3.32-13.10). Similar results were shown in Nt-proBNP(+) MIF(+) group with regard to the risk of MACE (FIG. 5 & Table 6).

TABLE 6

Univariate Cox regression for All-cause mortality and MACE in STEMI patients grouped according to MIF, Nt-proBNP or hs-TnT peak in high fertile separately.

|  | Combined Groups | Univariate Cox regression | |
|---|---|---|---|
|  |  | HR(95% CI) | P value |
| All-cause mortality | Nt-proBNP(−) MIF(−) | 1.00 | |
|  | Nt-proBNP(+) MIF(+) | 11.28 (4.82-26.94) | <0.001 |
|  | Nt-proBNP (−) TnT peak(−) | 1.00 | |
|  | Nt-proBNP(+) TnT peak(+) | 6.60 (3.32-13.10) | <0.001 |
|  | MIF (−) TnT peak(−) | 1.00 | |
|  | MIF(+) TnT peak(+) | 4.12 (2.16-7.85) | <0.001 |
|  | Triple (−) | 1.00 | |
|  | Triple (+) | 11.39 (4.29-29.68) | <0.001 |
| MACE | Nt-proBNP (−) MIF(−) | 1.00 | <0.001 |
|  | Nt-proBNP(+) MIF(+) | 5.07 (3.31-7.76) | |
|  | Nt-proBNP (−) TnT peak(−) | 1.00 | <0.001 |
|  | Nt-proBNP(+) TnT peak(+) | 4.46 (2.94-6.76) | |
|  | MIF(−) TnT peak(−) | 1.00 | <0.001 |
|  | MIF(+) TnT peak(+) | 3.20 (2.19-4.95) | |
|  | Triple (−) | 1.00 | |
|  | Triple (+) | 5.54 (3.33-9.20) | <0.001 |

Patients grouped according to MIF, Nt-proBNP or hs-TnT peak in high tertile separately.

These findings demonstrate that in patients with STEMI admission MIF has prognostic value for adverse progression of LV systolic dysfunction, long-term mortality and MACE, independent of clinical established risk factors, acute LVEF and routinely measured biomarkers. In addition, admission MIF together with Nt-proBNP and/or hs-TnT facilitates a better prognostic prediction. The current study establishes admission MIF as a useful biomarker for short- and long-term prognosis in STEMI patients. Admission MIF can accordingly allow for risk stratification of high-risk STEMI patients, who may potentially benefit from more comprehensive diagnostic evaluation and more intensive therapy for secondary prevention. These findings establish the utility of biomarker-guided management strategies to patients who may have poor long-term prognosis.

First, we showed that admission MIF levels were predictive of later changes in necrotic markers (peak CK-MB and peak hs-TnT) and inflammatory parameters (hs-CRP, white blood cell count). Further, admission MIF is an independent risk factor of impaired restoration of myocardial reperfusion (ST-segment resolution <50% by 60 min post-PCI). Second, recovery in LVEF by 12 months post-STEMI was impaired in subgroup with a high MIF level. Third, by multivariate analysis, admission MIF as a continuous variable remained an independent predictor of long-term all-cause mortality, cardiovascular death and MACE after adjustments for established risk factors and biomarkers. Finally, we demonstrated in our STEMI patients that risk stratification of all-cause mortality and MACE was improved by combination of MIF and day-3 Nt-proBNP. These findings suggest that admission MIF level provides useful information beyond what currently is available from clinical and angiographic characteristics in patients with STEMI.

Myocardial ischaemia/reperfusion injury remains a common event in patients with STEMI. Despite optimal angiographic revascularization, microvascular damage, manifested in the form of no-reflow phenomenon, is detected in 30-60% of STEMI patients. We have now shown that patients presenting with an initial MIF in the high tertile have a 2.5-fold greater prevalence of incomplete ST-segment resolution compared with those in the low tertile, and that MIF was an independent predictive risk factor of incomplete ST-segment resolution. This is the first demonstration that level of plasma MIF prior to primary PCI is predictive of reperfusion efficacy and microvascular obstruction. The ability of admission MIF level to predict reperfusion damage may contribute to its infarct size predictive nature.

The invention claimed is:

1. A method of treating acute coronary syndrome (ACS) in a subject, the method comprising:
   determining the concentration of:
   (a) macrophage migration inhibitory factor (MIF), and
   (b) N-terminal prohormone of brain natriuretic peptide (Nt-proBNP), or brain natriuretic peptide (BNP),
   in a sample from the subject, wherein the sample is blood, plasma or serum,
   comparing the concentration of MIF to a reference MIF concentration, wherein the reference MIF concentration is at least 70 ng/ml,
   comparing the concentration of Nt-proBNP (or BNP) to a reference Nt-proBNP (or BNP) concentration, wherein the reference Nt-proBNP (or BNP) concentration is at least 700 pg/mL, and
   performing percutaneous coronary intervention (PCI) and/or fibrinolysis on the subject when the concentrations of MIF and Nt-proBNP (or BNP) from the sample are equal to or higher than the reference concentrations of MIF and Nt-proBNP (or BNP),
   thereby treating the subject having ACS.

2. The method according to claim 1, further comprising determining the concentration of troponin in a sample from the subject, wherein the sample is blood, plasma or serum.

3. The method according to claim 2, wherein the concentrations of MIF, Nt-proBNP (or BNP) and/or troponin are determined from plasma.

4. The method according to claim 1, wherein ACS is acute myocardial infarction (AMI).

5. The method according to claim 4, wherein the AMI is ST elevation myocardial infarction (STEMI).

6. The method according to claim 1, comprising determining MIF concentration of the subject in a sample taken less than 4 hours after symptom onset.

7. The method according to claim 6, wherein the sample is taken 3 hours or less, 2 hours or less, 1 hour or less, or 30 minutes or less after symptom onset.

8. The method according to claim 2, wherein the troponin is high sensitive-troponin T (hs-TnT).

9. The method according to claim 1, wherein Nt-proBNP (or BNP) and MIF are measured in the same sample.

10. The method according to claim 2, further comprising comparing the concentration of troponin from the sample from the subject to a reference troponin concentration, wherein the reference troponin concentration is at least 4.5 ng/ml,
    wherein the percutaneous coronary intervention (PCI) and/or fibrinolysis is performed on the subject when the concentration of troponin from the sample is equal to or higher than the reference troponin concentration,
    thereby treating the subject having ACS.

11. The method according to claim 1, wherein the reference concentration of Nt-proBNP (or BNP) is at least 1200 pg/ml.

12. The method according to claim 1, wherein the concentration of BNP is determined in plasma derived from a blood sample obtained from a patient 3 days following symptom onset.

13. The method according to claim 2, further comprising determining the concentration of another biomarker selected from the group consisting of myoglobin, creatine kinase (CK) or C reactive protein (CRP).

14. The method according to claim 1, wherein the reference concentration of MIF is at least 73 ng/ml.

* * * * *